US011774418B2

United States Patent
Martin et al.

(10) Patent No.: US 11,774,418 B2
(45) Date of Patent: Oct. 3, 2023

(54) TECHNIQUES FOR EXCEPTION-BASED VALIDATION OF ANALYTICAL INFORMATION

(71) Applicant: WATERS TECHNOLOGIES IRELAND LIMITED, Dublin (IE)

(72) Inventors: Nathaniel Martin, Stockport (GB); David Eatough, Heaviley (GB); Iain Monks, Lymm-Warrington (GB); Stephen Jepson, Sale (GB); Steve Leicester, Manchester (GB)

(73) Assignee: WATERS TECHNOLOGIES IRELAND LIMITED, Dublin (IE)

( * ) Notice: Subject to any disclaimer, the term of this patent is extended or adjusted under 35 U.S.C. 154(b) by 471 days.

(21) Appl. No.: 17/012,730

(22) Filed: Sep. 4, 2020

(65) Prior Publication Data

US 2021/0063362 A1 Mar. 4, 2021

Related U.S. Application Data

(60) Provisional application No. 62/895,751, filed on Sep. 4, 2019.

(51) Int. Cl.
*G01N 30/86* (2006.01)
*G01N 30/72* (2006.01)

(52) U.S. Cl.
CPC ......... *G01N 30/8693* (2013.01); *G01N 30/72* (2013.01); *G01N 30/8631* (2013.01); *G01N 30/8696* (2013.01)

(58) Field of Classification Search
CPC . G01N 30/8693; G01N 30/72; G01N 30/8631
See application file for complete search history.

(56) References Cited

U.S. PATENT DOCUMENTS

| 2008/0015793 A1* | 1/2008 | Ben-Menahem | G01N 31/00 702/30 |
| 2011/0177964 A1* | 7/2011 | Broach | G16C 20/64 506/18 |

(Continued)

OTHER PUBLICATIONS

International Search Report and Written Opinion for International application No. PCT/IB2020/058270, dated Dec. 15, 2020, 14 pages.

(Continued)

*Primary Examiner* — Ricky Go
(74) *Attorney, Agent, or Firm* — Goodwin Procter LLP

(57) ABSTRACT

Techniques and apparatus for information assessment processes are described. In one embodiment, for example, a computer-implemented method for performing a review-by-exception process may include, via one or more processors of a computing device, accessing chromatography information generated via analyzing a sample using a mass spectrometry system, the chromatography information comprising at least one peak and at least one peak attribute for the at least one peak, determining posterior probability information for the chromatography information; generating an estimated peak model based on the posterior probability information, determining a confidence indicator for the estimated peak model, and generating an exception for the at least one peak responsive to the confidence indicator being outside of an exception threshold. Other embodiments are described.

20 Claims, 20 Drawing Sheets

(56) References Cited

U.S. PATENT DOCUMENTS

2012/0271556 A1* 10/2012 Szacherski ............. G16B 40/10
702/22
2016/0217986 A1* 7/2016 Denny ................ H01J 49/0036
2020/0185063 A1* 6/2020 Narain .................. G01N 33/48

OTHER PUBLICATIONS

Hibbert, D.B., et al., "An introduction to Bayesian methods for analyzing chemistry data Part II: A review of application os Bayesian methods in chemistry", Chemometrics and Intelligent Laboratory Systems 97(2):211-220 (2009).
Armstrong, N., et al., "An introduction to Bayesian methods for analyzing chemistry data", 97(2):194-210 (2009).
Skilling, J., "Nested sampling for general Bayesian computation", Journal of Bayesian Analysis, 1(4):833-860 (2006).

\* cited by examiner

TECHNIQUES FOR EXCEPTION-BASED VALIDATION OF ANALYTICAL INFORMATION

CROSS-REFERENCE TO RELATED APPLICATIONS

This application claims the benefit of and priority to U.S. Provisional Patent Application No. 62/895,751, filed on Sep. 4, 2019, the entire contents of which is hereby incorporated by reference.

TECHNICAL FIELD

Embodiments herein generally relate to managing analytical information generated via performance of a method using an analytical device, and, more particularly, to processes for reviewing the analytical information to validate operation of the method and/or the analytical device.

BACKGROUND

The performance of analytical instruments is continually monitored to ensure data quality. For example, analysts may perform various quality assurance processes, such as system calibrations and/or quality control checks, to validate proper system operation. Mass analysis instruments, such as mass spectrometry (MS) and/or liquid chromatography-mass spectrometry (LC-MS) systems, are capable of providing detailed characterization of complex sample sets, but typically require long turn-around-times. Accordingly, analysts need to be able to perform quality assurance tests and resolve issues with mass analysis devices in an efficient and cost-effective manner to maximize throughput.

A typical mass analysis method may generate a large amount of analytical information. For example, an MS method may generate hundreds or even thousands of chromatograms. The analytical information for quality assurance samples (for instance, blanks, calibration samples, standards, and/or the like) must be reviewed to ensure quality of sample component measurements. However, conventional systems provide inefficient and convoluted pathways to access and review the analytical information. Therefore, quality assurance of MS methods in conventional systems are a major bottleneck that negatively effects productivity.

DETAILED DESCRIPTION

Figure 1:
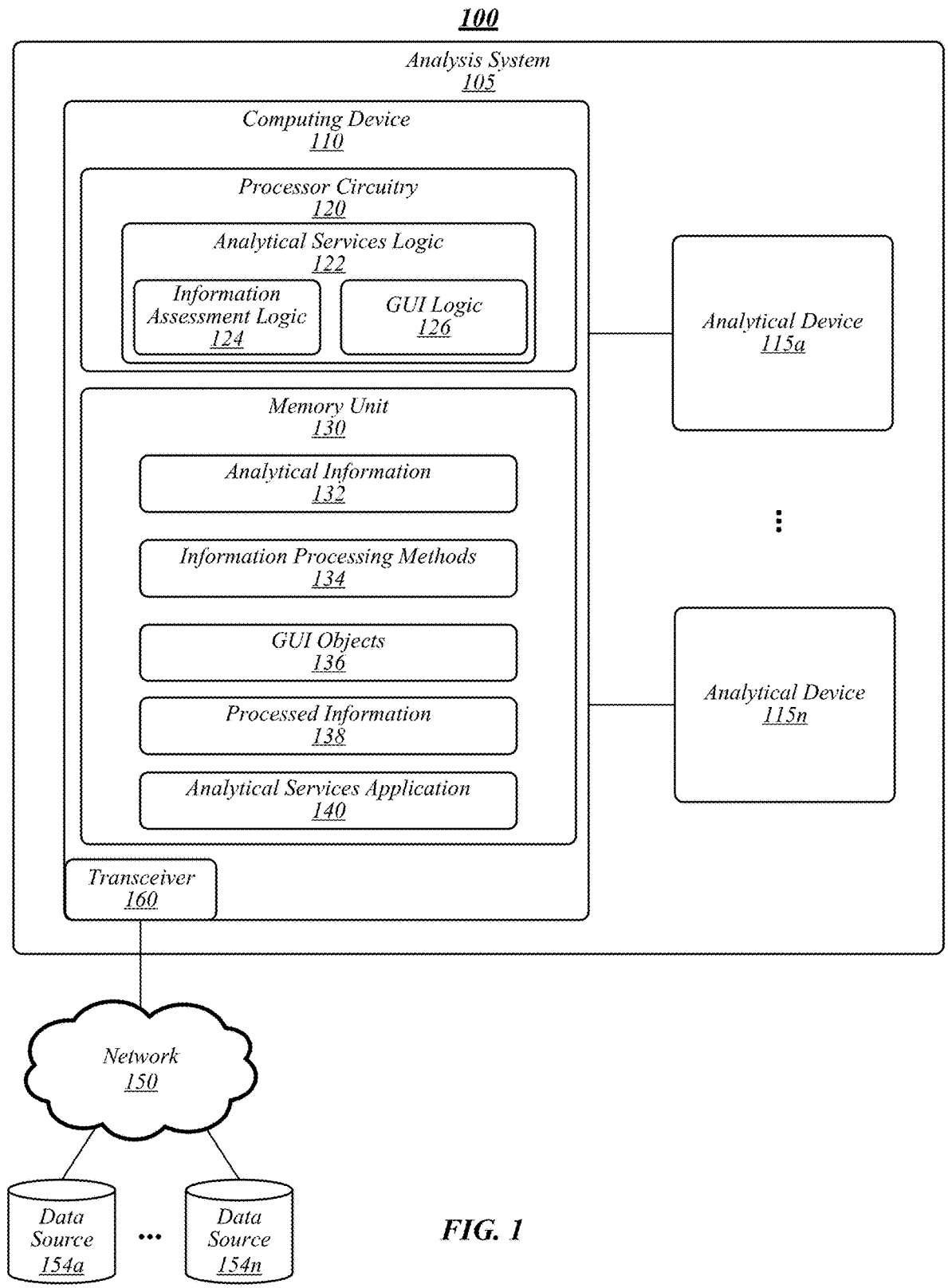
FIG. 1 illustrates an embodiment of a first operating environment.

Various embodiments may generally be directed toward systems, methods, and/or apparatus for generating, controlling, processing, operating, or otherwise managing analytical information for analytical systems. In some embodiments, a data assessment process may operate to process analytical information associated with an analytical system, such as an analyte or sample analysis, sample injection, sample list, batch, analytical method, run, experiment, quality control analysis, and/or the like. In some embodiments, a data assessment process may include providing analytical information to a user to facilitate review of the analytical information for quality assurance purposes, such as determining whether a quality control sample or analyte is within expected limits. In various embodiments, the data assessment process may present graphical user interface (GUI) objects operative to enable efficient and accurate review of analytical information. In exemplary embodiments, the GUI objects may implement an exception-based (or "review-by-exception") quality assurance review process.

In some embodiments, an information assessment process may include a method of data analysis (or information assessment) that involves acquiring (in real-time or substantially real-time) and/or importing analytical information (for instance, from a pre-existing sample analysis or sample list). The information assessment process may include selecting an information processing method for processing the analytical information. In various embodiments, an information processing method may include various data processing parameters, output information (for instance, plots, graphs, tables, integrations, and/or the like), quality control limits or thresholds (for instance, including thresholds/limits specific for each particular level), and/or the like that may be used to process analytical information, for example, resulting from analysis of a sample using an analytical system.

For example, an analytical system may include a mass analysis system, such as a mass spectrometry (MS) or liquid-chromatography (LC)-MS (LC-MS) system. Although MS or LC-MS systems are described in some examples, embodiments are not so limited, as any application capable of operating according to some embodiments is contemplated herein. In some embodiments, an information assessment process may include a method of data analysis that includes acquiring and/or importing analytical information (for instance, MS information) and selecting a data processing method to process the analytical information. In various embodiments, data acquisition and/or information assessment may be or may include MS quantitation of MS-acquired data. In some embodiments, the MS-acquired data may be or may include information generated via a multiple reaction monitoring (MRM) analysis.

In various embodiments, the information assessment process may operate to supplement any missing values, for example, based on historical information, values provided in the data processing method, extrapolation, combinations thereof, and/or the like. In some embodiments, the data processing method may operate to determine exceptions in the analytical information. In general, an exception may include any value outside of a predetermined value or range. For example, the expected value for a certain quality control (QC) analyte may be x and an exception may be generated if the detected value of the QC analyte is outside of x+/−(exception range or percentage) (for instance, 20%). In various embodiments, the information assessment process may operate to present a plurality of data sets for components of the analytical information (analytical components), such as for each sample, analyte, injection, QC analyte or sample, and/or the like. In exemplary embodiments, a user may flag an exception, for example, based on a visual inspection that is not automatically triggered by information assessment process.

For example, in some embodiments, the information assessment process may present GUI objects presenting various graphs, charts, plots, error bars, and/or the like for each analyte (see, for example, FIGS. 3A-7E). In conventional systems, plots for different analytical components generally have Y-axes and/or X-axes scaled for specific ranges, making visual comparison across different components difficult if not practically impossible. Accordingly, in some embodiments, all or substantially all plots may have the same or substantially the same Y-axis and/or X-axis values (for instance, fixed limits on one or more axes of each plot), for instance, to facilitate efficient visual comparison across different analytical components.

One non-limiting example of a plot for MS analytical information may include a percent deviation from known data points (for instance, concentration) for each analyte. In various embodiments, each plot may highlight deviations from expected values, for example, via GUI objects presenting deviations having a different presentation characteristic than expected or non-deviating values. Non-limiting examples of presentation characteristics may include shape, color, size, symbol, and/or the like. Another non-limiting example of a plot for MS analytical information may include plotting chromatograms for blanks against a limit of quantitation (for instance, LLOQ or the lowest detected standard not excluded by a user). In some embodiments, a plot of blanks against LLOQ may include indications of plots that have integrated regions against a selected analyte.

Further non-limiting examples of plots for MS analytical information may include plots of response deviation and/or retention time deviation, indicating, for example, standards, blanks, QC samples, and unknowns with different presentation characteristics. Additional non-limiting examples of plots for MS analytical information may include plots of peak integrations for all injections for selected analytes.

In various embodiments, integration settings for analytical components (for instance, specific internal standards) may be modified, for example, to change a plot, address an exception, and/or the like. In various embodiments, Y-axes and/or X-axes for plots with modified integration settings may be reset, for example, depending on modified injection settings. In some embodiments, an audit trail may be generated for any change to analytical information and/or the presentation thereof via a GUI object (for instance, altering integration settings for a standard). In exemplary embodiments, an exceptions GUI object (for instance, a toggle button) may be provided to allow a user to select for presentation of exceptions only. In some embodiments, a display category GUI object may be provided to allow a user to filter for presentation of certain categories of analytical components, such as unknowns, blanks, standards, QCs, and/or the like.

In various embodiments, the information assessment process may operate to determine a confidence (or uncertainty) value or indication for analytical information. In some embodiments, the confidence (or uncertainty) indication may be or may include comparison(s) of multiple plots of the same information using different models (for instance, a Gaussian model and a Bayesian model) and/or error bars. In various embodiments, analytical information associated with a certain level of confidence or uncertainty (for instance, below a threshold value) may be flagged as an exception requiring review (for instance, as part of a review-by-exception process).

Typically operating within a regulated environment, analysts using MS or similar technology to identify compounds in a complex sample are obligated to ensure that the peak integration algorithm has performed satisfactorily, which generally involves visual inspection of the peak and integration results. Clearly this can be very time consuming with the amount of information generated via an MS-based analysis. Therefore, various information assessment processes may include review-by-exception methods configured according to some embodiments. In some embodiments, the information assessment processes may involve using some of the peak attributes and flagging any results for which those attributes lie outside some threshold. The flagged elements may be deemed exceptional and flagged for review, thus reducing considerably the quality review required by an analyst.

Analytical information assessment processes according to some embodiments may provide multiple technological advantages, including improvements to computing technology, over conventionally systems and methods. The ability to access analytical information and draw simple conclusions from new or pre-existing data accurately and efficiently is an important aspect of the perceived usability of analytical systems, including MS and LC-MS systems. Conventional systems typically provide difficult and convoluted pathways to data that hinder the ability of a user to efficiently and effectively visualize information regarding the function or performance of their system (for instance, quality assurance exceptions and how to address exceptions), which leads to frustrations and an overall negative impression of such conventional analytical tools. Accordingly, some embodiments provide analytical information assessment processes operating using visual tools to allow users to obtain efficient and effective visualization of analytical information associated with an analytical system, method, analyte, and/or the like. Analytical information assessment processes according to some embodiments may allow a user to perform assessments and comparisons (for instance, implemented via exception-based review processes) that is independent of the data source.

For example, some embodiments may allow an analyst to resolve issues with an analytical system in an efficient and cost-effective manner to optimize throughput, compared with conventional systems and processes. An analyst/reviewer may be able to review the results generated from an analyses to determine their validity, for example, via an efficient process of reviewing a large volume of analytical information (for instance, 30,000+ chromatograms). More specifically, an analyst/reviewer may be able to identify outliers and unexpected results via visually exception-based inspection of the processed data/results, which operates to significantly reduce the amount of information requiring review. In addition, exception-based review processes according to some embodiments may operate to provide a level of confidence in reported measurements, allow a review-by-exception workflow based, for instance, on a level of confidence rather than hard peak property thresholds, require less expertise from an analyst (for example, the analyst does not need to judge the quality of the result as the review-by-exception process may provide this information, and/or avoid the need for manual intervention (for example, processes may report the result as-is and poor results may be due to poor or insufficient data and not something which can be overcome by ad hoc, manual intervention). Other advantages are described and/or would be known to those of ordinary skill in the art based on the present disclosure.

In the following description, references to "one embodiment," "an embodiment," "example embodiment," "various embodiments," etc., indicate that the embodiment(s) of the technology so described may include particular features, structures, or characteristics, but more than one embodiment may and not every embodiment necessarily does include the particular features, structures, or characteristics. Further, some embodiments may have some, all, or none of the features described for other embodiments.

As used in this description and the claims and unless otherwise specified, the use of the ordinal adjectives "first," "second," "third," etc. to describe an element merely indicate that a particular instance of an element or different instances of like elements are being referred to, and is not intended to imply that the elements so described must be in a particular sequence, either temporally, spatially, in ranking, or in any other manner.

FIG. 1 illustrates an example of an operating environment 100 that may be representative of some embodiments. As shown in FIG. 1, operating environment 100 may include an analysis system 105 operative to manage analytical data associated with analytical devices 115a-n. In some embodiments, analytical devices 115a-n may be or may include a chromatography system, a liquid chromatography (LC) system, a gas chromatography (GC) system, a mass analyzer system, a mass spectrometer (MS) system, an ion mobility spectrometer (IMS) system, a high-performance liquid chromatography (HPLC) system, a ultra-performance liquid chromatography (UPLC®) system, a ultra-high performance liquid chromatography (UHPLC) system, a solid-phase extraction system, a sample preparation system, a heater (for example, a column heater), a sample manager, a solvent manager, an in vitro device (IVD), combinations thereof, components thereof, variations thereof, and/or the like. Although LC, MS, and LC-MS are used in examples in this detailed description, embodiments are not so limited, as other analytical devices capable of operating according to some embodiments are contemplated herein.

In some embodiments, computing device 110 may be communicatively coupled to analytical devices 115a-n. In other embodiments, computing device 110 may not be communicatively coupled to analytical devices 115a-n. Computing device 110 may obtain analytical information 132 directly from data sources 154a-n and/or directly from analytical devices 115a-n. In some embodiments, computing device 110 may be or may include a standalone computing device, such as a personal computer (PC), server, tablet computing device, cloud computing device, and/or the like. In some embodiments, computing device 110 may be a separate device from analytical devices 115a-n. In other embodiments, computing device 110 may be a part, such as an integrated controller, of analytical devices 115a-n.

As shown in FIG. 1, computing device 110 may include processing circuitry 120, a memory unit 130, and a transceiver 160. Processing circuitry 120 may be communicatively coupled to memory unit 130 and/or transceiver 160.

Processing circuitry 120 may include and/or may access various logic for performing processes according to some embodiments. For instance, processing circuitry 120 may include and/or may access analytical services logic 122, information assessment logic 124, and/or GUI logic 126. Processing circuitry and/or analytical services logic 122, information assessment logic 124, and/or GUI logic 126, or portions thereof, may be implemented in hardware, software, or a combination thereof. As used in this application, the terms "logic," "component," "layer," "system," "circuitry," "decoder," "encoder," and/or "module" are intended to refer to a computer-related entity, either hardware, a combination of hardware and software, software, or software in execution, examples of which are provided by the exemplary computing architecture 1000. For example, a logic, circuitry, or a layer may be and/or may include, but are not limited to, a process running on a processor, a processor, a hard disk drive, multiple storage drives (of optical and/or magnetic storage medium), an object, an executable, a thread of execution, a program, a computer, hardware circuitry, integrated circuits, application specific integrated circuits (ASIC), programmable logic devices (PLD), digital signal processors (DSP), field programmable gate array (FPGA), a system-on-a-chip (SoC), memory units, logic gates, registers, semiconductor device, chips, microchips, chip sets, software components, programs, applications, firmware, software modules, computer code, combinations of any of the foregoing, and/or the like.

Although analytical services logic 122 is depicted in FIG. 1 as being within processing circuitry 120, embodiments are not so limited. In addition, although information assessment logic 124 and GUI logic 126 are depicted as being a logic of analytical services logic 122, embodiments are not so limited, as information assessment logic 124 and GUI logic 126 may be separate logics and/or may not be standalone logics but, rather, a part of analytical services logic 122. For example, analytical services logic 122, and/or any component thereof, may be located within an accelerator, a processor core, an interface, an individual processor die, implemented entirely as a software application (for instance, analytical services application 140) and/or the like.

Memory unit 130 may include various types of computer-readable storage media and/or systems in the form of one or more higher speed memory units, such as read-only memory (ROM), random-access memory (RAM), dynamic RAM (DRAM), Double-Data-Rate DRAM (DDRAM), synchronous DRAM (SDRAM), static RAM (SRAM), programmable ROM (PROM), erasable programmable ROM (EPROM), electrically erasable programmable ROM (EEPROM), flash memory, polymer memory such as ferroelectric polymer memory, ovonic memory, phase change or ferroelectric memory, silicon-oxide-nitride-oxide-silicon (SONOS) memory, magnetic or optical cards, an array of devices such as Redundant Array of Independent Disks (RAID) drives, solid state memory devices (e.g., USB memory, solid state drives (SSD) and any other type of storage media suitable for storing information. In addition, memory unit 130 may include various types of computer-readable storage media in the form of one or more lower speed memory units, including an internal (or external) hard disk drive (HDD), a magnetic floppy disk drive (FDD), and an optical disk drive to read from or write to a removable optical disk (e.g., a CD-ROM or DVD), a solid state drive (SSD), and/or the like.

Memory unit 130 may store an analytical services application 140 that may operate, alone or in combination with analytical services logic 122, to perform various functions according to some embodiments.

In various embodiments, analytical services application 140 may operate to perform, execute, implement, support, or otherwise facilitate information assessment processes according to some embodiments. In some embodiments, for example, analytical services application 140 may provide GUI objects, screens, pages, windows, and/or the like for facilitating information assessment processes (see, for example, FIGS. 2-6D).

In exemplary embodiments, analytical services application 140 may allow for selection of analytical information 132, for example, associated with an analytical component (for instance, a sample analysis and associated quality assurance samples or analytes, such as blanks, standards, QCs, and/or the like). For example, analytical services application 140 may allow for selection of an analytical information object (for instance, a file) that includes data associated with a sample analysis, which may include, for instance, quality assurance analytes (or injections) and sample analytes (or injections).

In some embodiments, analytical information 132 may be or may include an object or other structure, such as a data file. Non-limiting examples of analytical information objects (or files) may include raw data files, processed data files, export package files, combinations thereof, and/or the like. For example, analytical information objects may include comma-delimited files (*.csv), Microsoft® Excel® files (*.xls, *.xlsx, and/or the like), MS software raw data files (for example, *.raw MassLynx™ files developed by Waters Corporation of Milford, Mass., United States), UNIFI export package files (*.uep) developed by the Waters Corporation, combinations thereof, and/or the like. Embodiments are not limited in this context. In some embodiments, an analytical information object may include information from a pre-existing analysis. In some embodiments, an analytical information object may include a data stream, such as a live or substantially live data stream from an analytical instrument, server, network, and/or the like.

Figure 2:
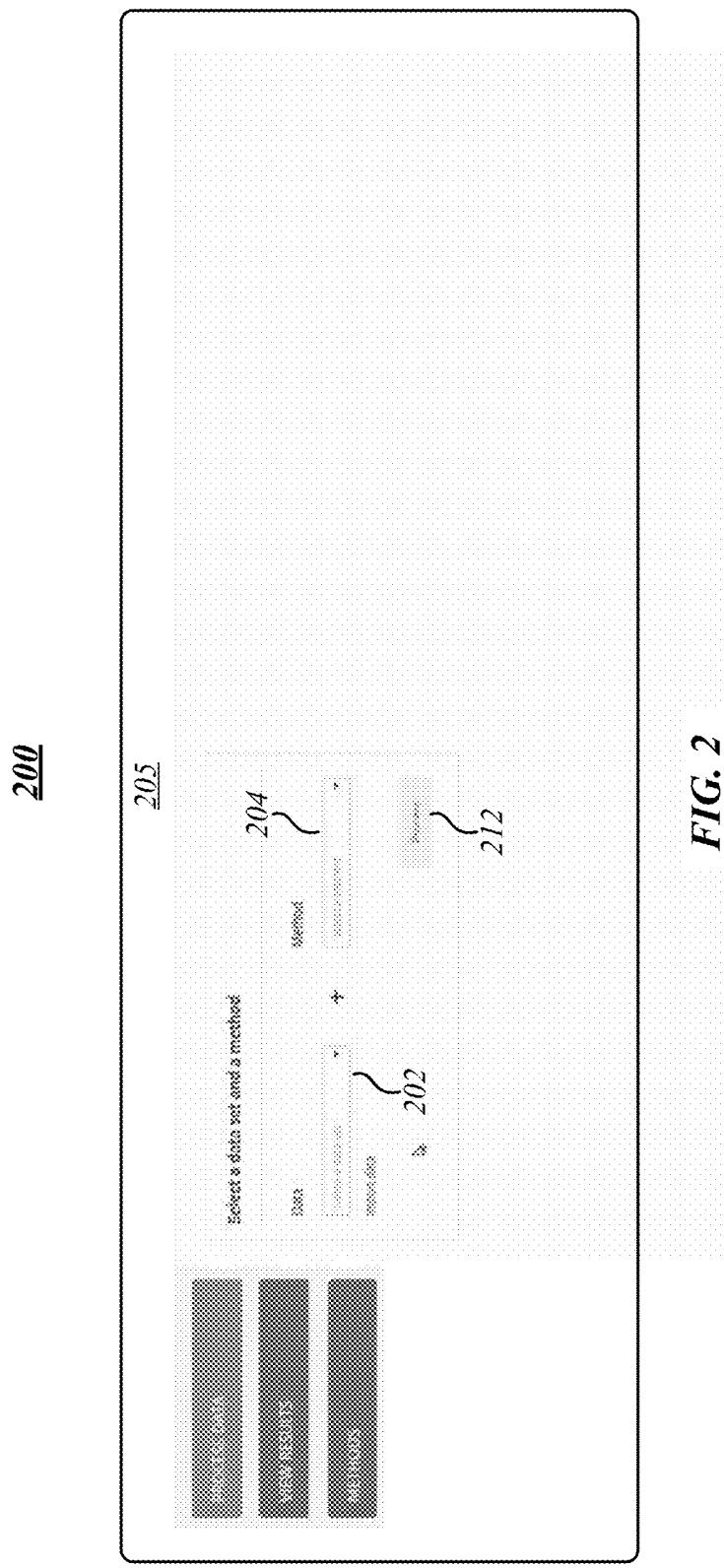
FIG. 2 illustrates an embodiment of a second operating environment.

FIG. 2 illustrates an example of an operating environment 200 that may be representative of some embodiments. As shown in FIG. 2, operating environment 200 may include an information processing selection screen 205. In various embodiments, information processing selection screen 205 may present various GUI objects, such as an analytical information selection object 202 and an information processing method selection object 204. In various embodiments, analytical information selection object 202 may be used to access pre-existing information, such as analytical information generated during a previous analysis.

In various embodiments, analytical services application 140 may allow for selection of an information processing method 134 for processing analytical information 132 within a selected analytical information object. In general, an information processing method 134 may include information, parameters, rules, thresholds, integration parameters, and/or the like for processing analytical information 132 of a selected analytical information object. In some embodiments, information processing methods 134 may include quality control ranges, limits, thresholds, expected values/ranges, tolerances, and/or the like.

Analytical services application 140 may process analytical information 132 of a selected analytical information object according to a selected information processing method 134 to generate processed information 138. In various embodiments, processed information 138 may include analysis values (such as raw values) determined via an analysis (such as concentrations, mass-to-charge ratios, drift times, voltages (or other electrical signals that may be used to determine a value) and information resulting from processing, such as deviation percentages, exceptions, and/or the like. In some embodiments, analytical information may include gaps, missing values, and/or the like. For example, concentration information may be available at segments (for instance, times, levels, and/or the like) 1-3 and 6-10, but not segments 4 and 5. Accordingly, the concentration information for segments 4 and 5 may be determined to be missing values. In various embodiments, processed information 138 may include information generated to provide the missing values (gap information) through, for example, estimation, extrapolation, statistical analysis, and/or the like.

In various embodiments, processed information 138 may be used to generate GUI objects 136 for presentation to a user. In some embodiments, GUI objects 136 may allow a user to efficiently and effectively visualize the analytical information 132 associated with an analytical component, such as a sample run. For example, GUI objects 136 may highlight exceptions for a user, for example, to indicate quality control analytes that are outside of a range specified in a selected information processing method. In another example, GUI objects 136 may highlight gap information so that a user may differentiate actual values from gap information.

Referring to FIG. 2, selection of a proceed selection object 212 may cause analytical services application 140 to process a selected analytical information object based on a selected information processing method. The results of processing the analytical information object using the information processing method may be presented via various GUI objects, such as the screens and associated GUI objects depicted in FIGS. 3A-6D.

Figure 3A:
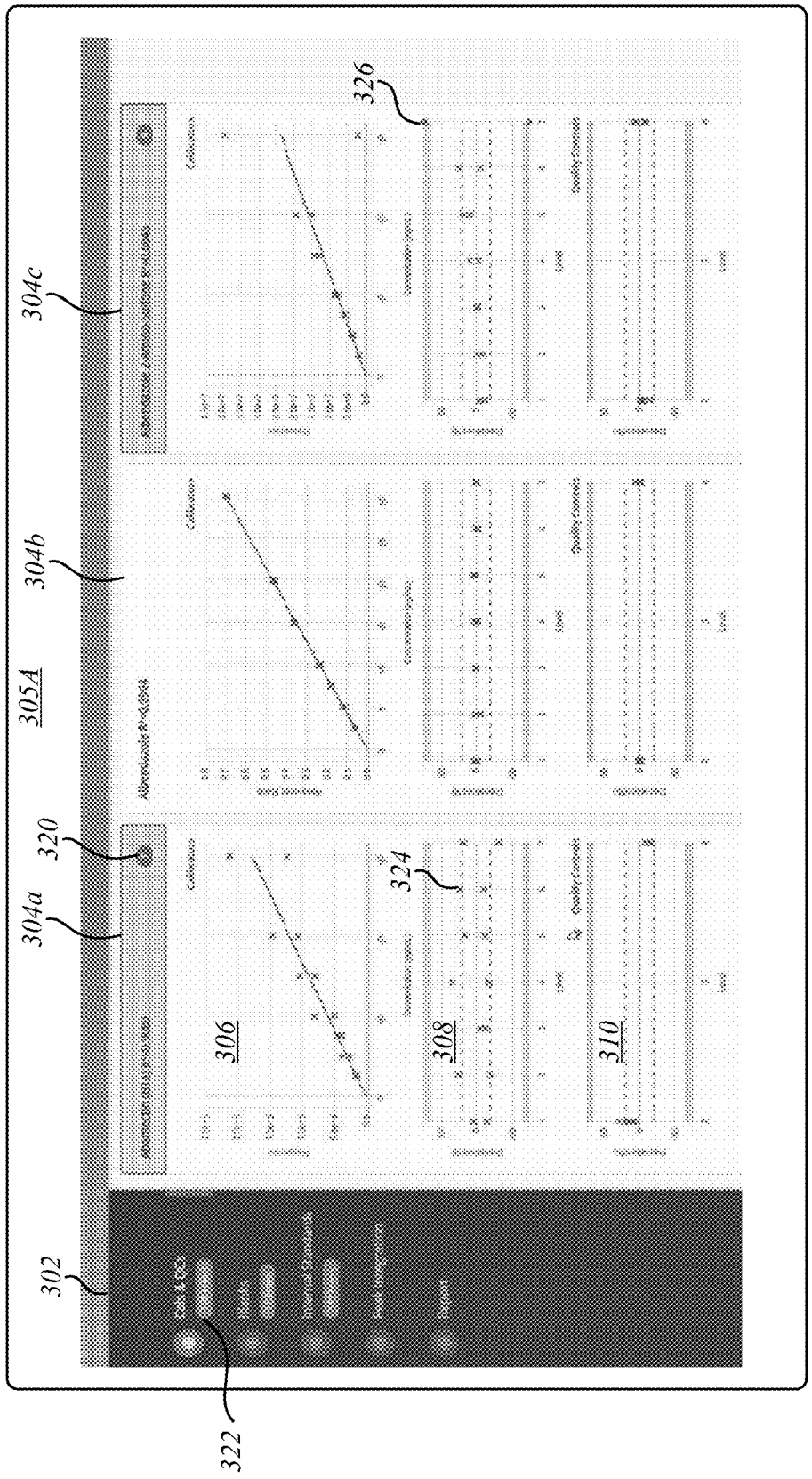
FIGS. 3A and 3B illustrate an embodiment of a third operating environment.
Figure 3B:
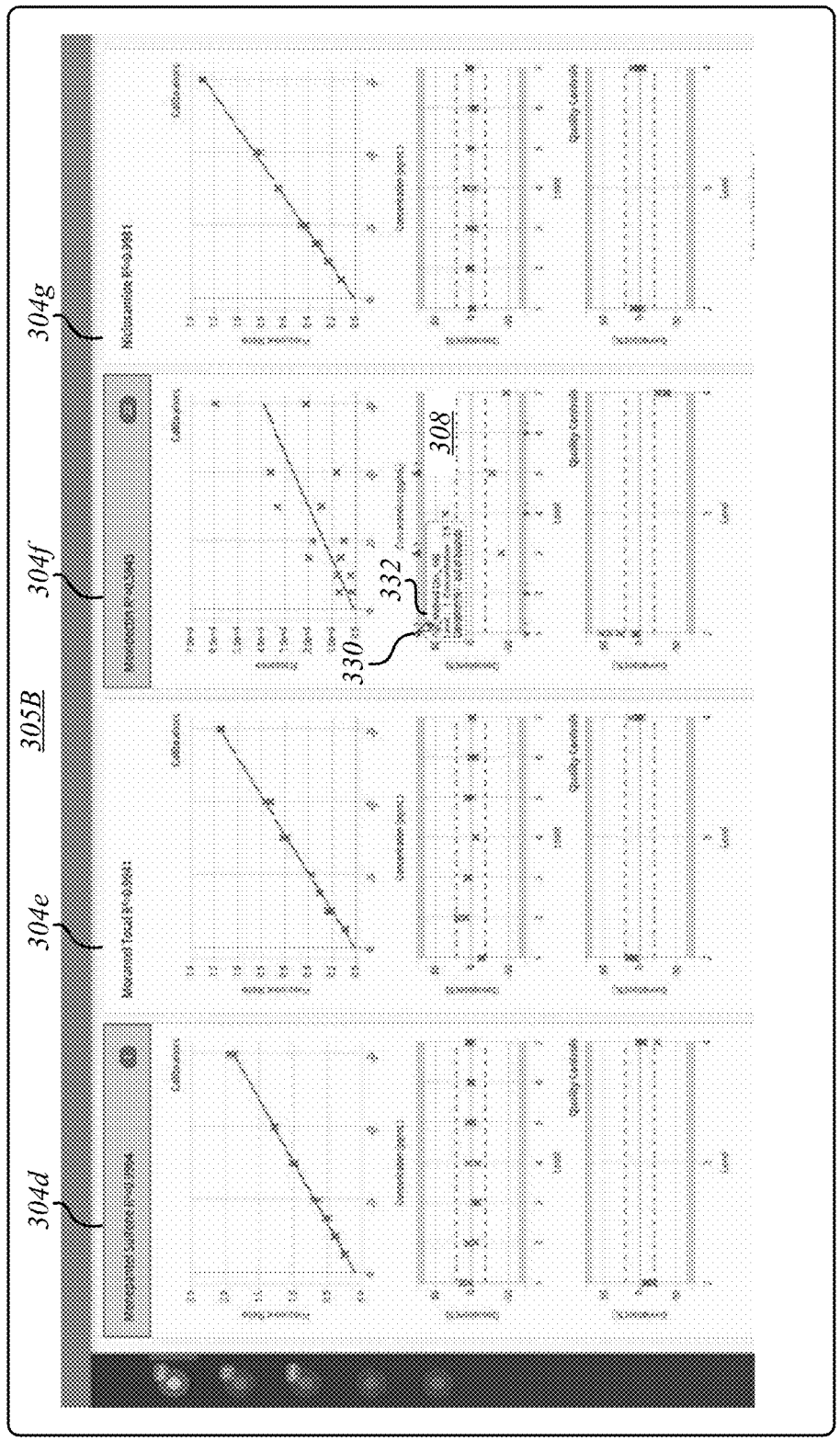

FIGS. 3A and 3B illustrate an example of an operating environment 300 that may be representative of some embodiments. As shown in FIG. 3A, operating environment 300 may include an information assessment screen or page 305A. In the embodiment of FIG. 3A, information assessment screen 305A may include a calibration and QC screen depicting calibration and QC information (for example, as information GUI objects) for various analytes 304a-c. In exemplary embodiments, information assessment screens 305A may include a navigation object 302 operable to allow selection of other information assessment screens associated with specified assessment categories, such as screens depicted in FIGS. 4A-6D. Non-limiting examples of assessment categories may include a blanks screen, an internal standards screen, a peak integration screen, and/or the like.

Information assessment processes according to some embodiments may implement an exception-based review process, for example, by presenting and highlighting exceptions to expected results in processed analytical information. In this manner, a user may focus on examining and/or addressing exceptions, allowing for a more efficient and focused review of analytical information compared with existing systems. Accordingly, in some embodiments, an information assessment screen 305A may present category-level exceptions 322 indicating exceptions for a particular category. In various embodiments, an information assessment screen 305A may present analyte-level exceptions 320 indicating exceptions for a particular analyte. In some embodiments, assessment-level exceptions 324, 326 may be presented indicating exceptions for a particular assessment 306, 308, 310 associated with an analyte. Non-limiting examples of assessments may include calibration curves 306, residuals plots 308, and quality controls 310. In some embodiments, one or more assessments may be presented as a plot, graph, chart, curve, and/or the like. For example, residual plots 308 and quality controls 310 may be presented as or substantially similar to Levy-Jennings charts having threshold or limit indicators (dashed lines). Values within the thresholds (for instance, normal or expected values) may have one or more presentation characteristics, such as shape, color, symbol, and/or the like. Exceptions 324, 326, or values outside of thresholds, may have one or more presentation characteristics to differentiate exceptions from expected values. In some embodiments, threshold limits may be fixed in an information processing method (for example, to comply with regulations, a standard operating procedure, and/or the like). In various embodiments, certain threshold limits may be configured. For example, threshold limits for residual plot 308 may be about 20% (for example, an information processing method may have a default of about 20%), which may be changed by a user to a different range.

As shown in FIGS. 3A and 3B, all or substantially all plots may have the same or substantially the same Y-axis and/or X-axis values (for example, fixed limits on one or more axes of each plot), for instance, to facilitate efficient visual comparison across different analytical components. For example, the Y-axis and X-axis for residual plots 308 for analytes 304a-g are the same. Accordingly, some values may be outside of the range of one or more of the axes. In such cases, an exception indicator 326, 330 may include a presentation characteristic to indicate that the actual value is outside of the range of one or more of the axes. For example, exception indicators 326, 330 are in the form of an arrow. In some embodiments, selection of exception indicator 326, 330 may allow for visualization of information associated with the actual value, for example, by presenting the actual value, expanding one or more of the axes, and/or the like. For example, selection of exception indictor 330 may cause presentation of an out-of-range value object 332 providing value information.

In various embodiments, a user may access information for various analytes by navigating or "paging through" analytes 304a-g. For example, FIG. 305A may present analytes 304a-c and activation of a navigation event may allow the user to move to the next set of analytes, for example, by presenting the next set of analytes 304d-g on screen 305B. FIGS. 3A and 3B depict all analytes, including analytes with an exception and analytes without an exception. In some embodiments, a user may select or toggle to only view analytes with an exception, such as analytes 304a, 304c, 304d, and 304f. Other selection or toggle options may be available according to some embodiments, such as toggling to only see analytes with calibration exceptions, residual exceptions, QC exceptions, and/or exceptions within a certain range (for instance, only exceptions deviating above a certain threshold), combinations thereof, and/or the like.

In various embodiments, a user may launch a workflow to address any exceptions presented via an information assessment screen, such as screens 305A and 305B. For example, selection of an assessment object 306, 308, 310 and/or portions thereof (for instance, a specific data point) may allow for an assessment modification, including, without limitation, modification of thresholds, curves, integration parameters, removal of a data point, and/or the like. In various embodiments, assessment modifications and any data associated therewith may be recorded, for example, in an audit trail.

As indicated by FIGS. 3A and 3B, information assessment processes according to some embodiments may allow a user to efficiently step through the analytes of a analysis method to check for certain primary quality assurance checks, such as calibrators, residuals, QCs, and/or the like and to proficiently make certain modifications to address any exceptions as allowed.

Figure 4A:
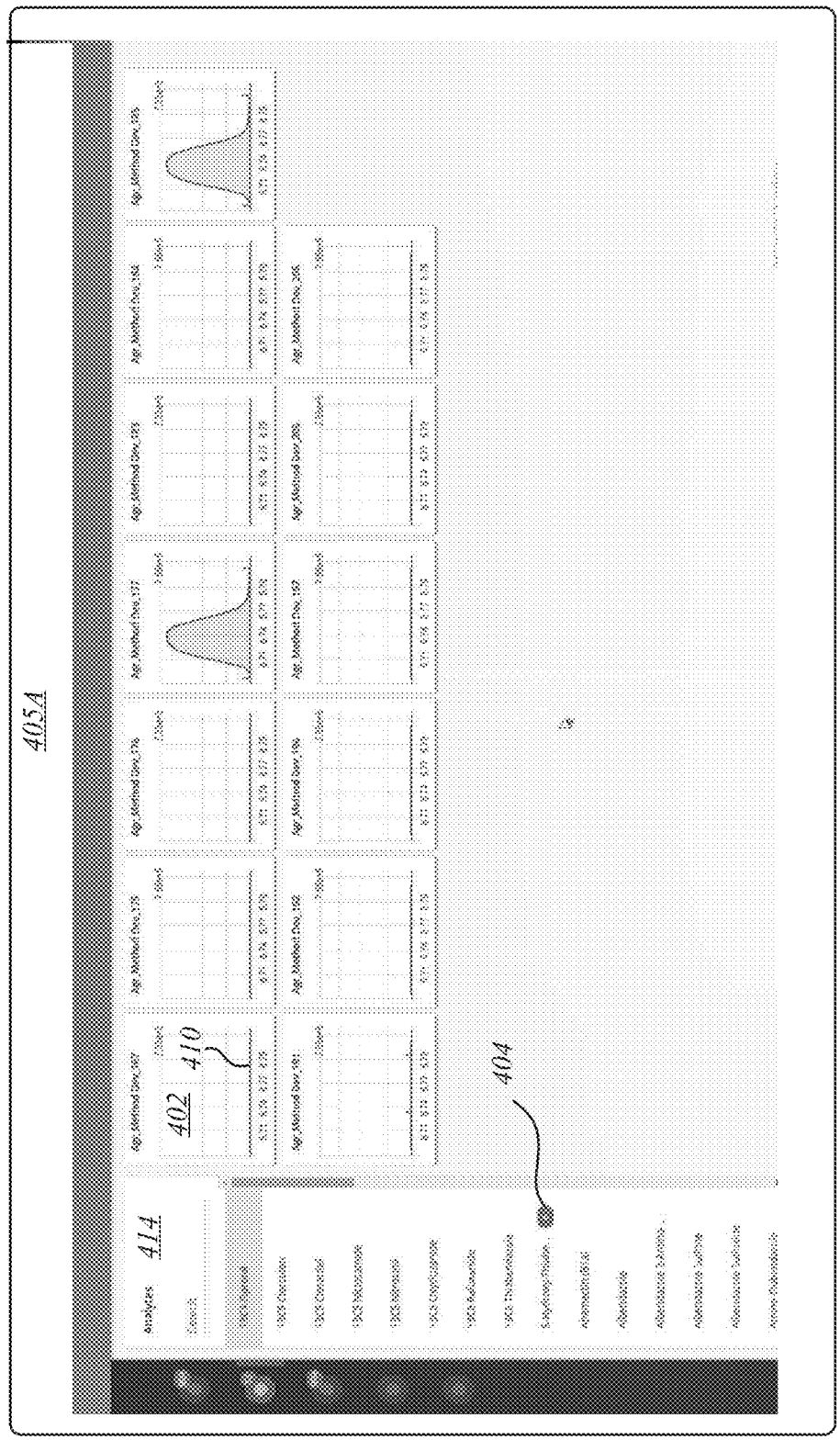
FIGS. 4A-4C illustrate an embodiment of a fourth operating environment.
Figure 4B:
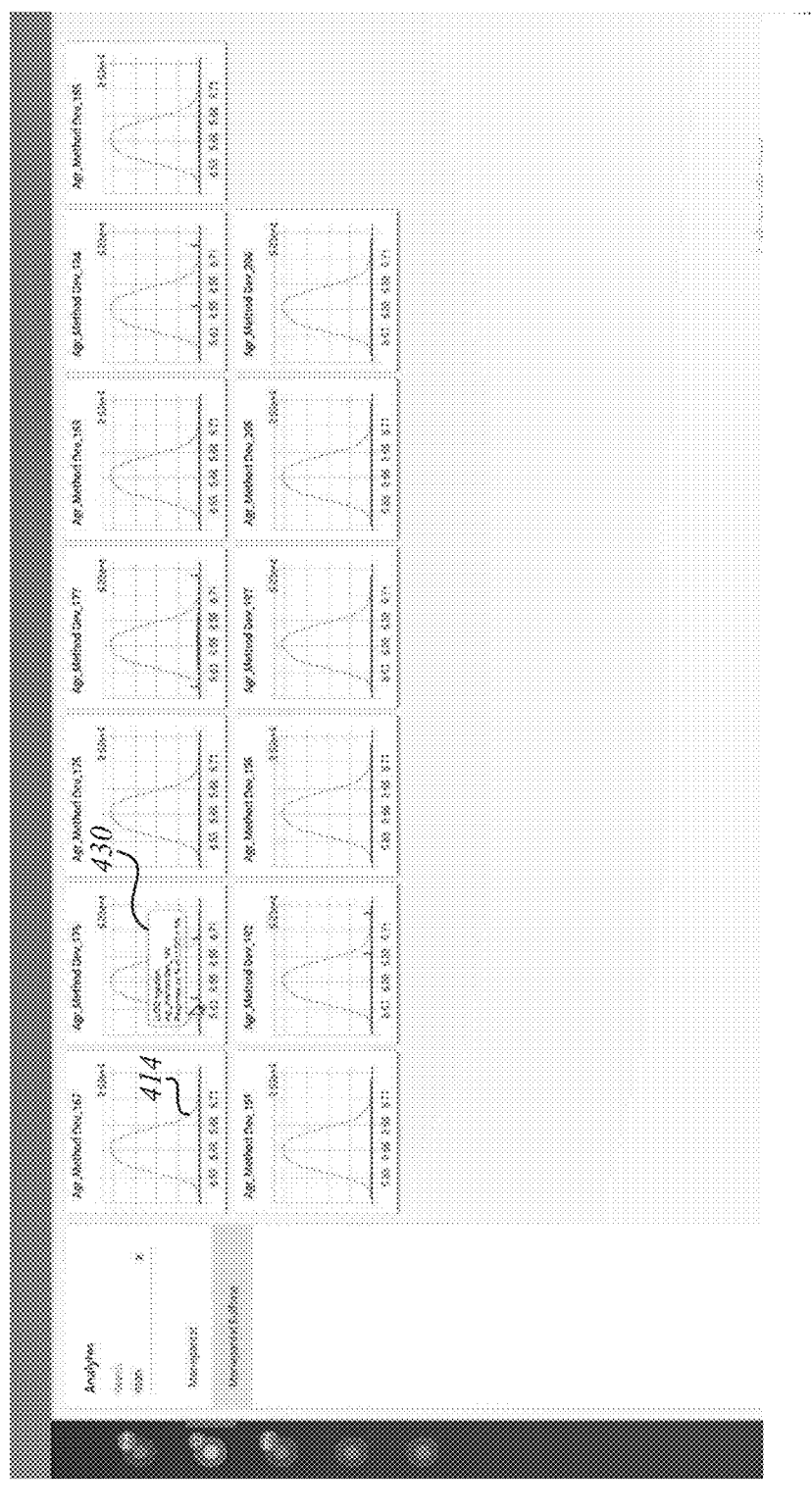
Figure 4C:
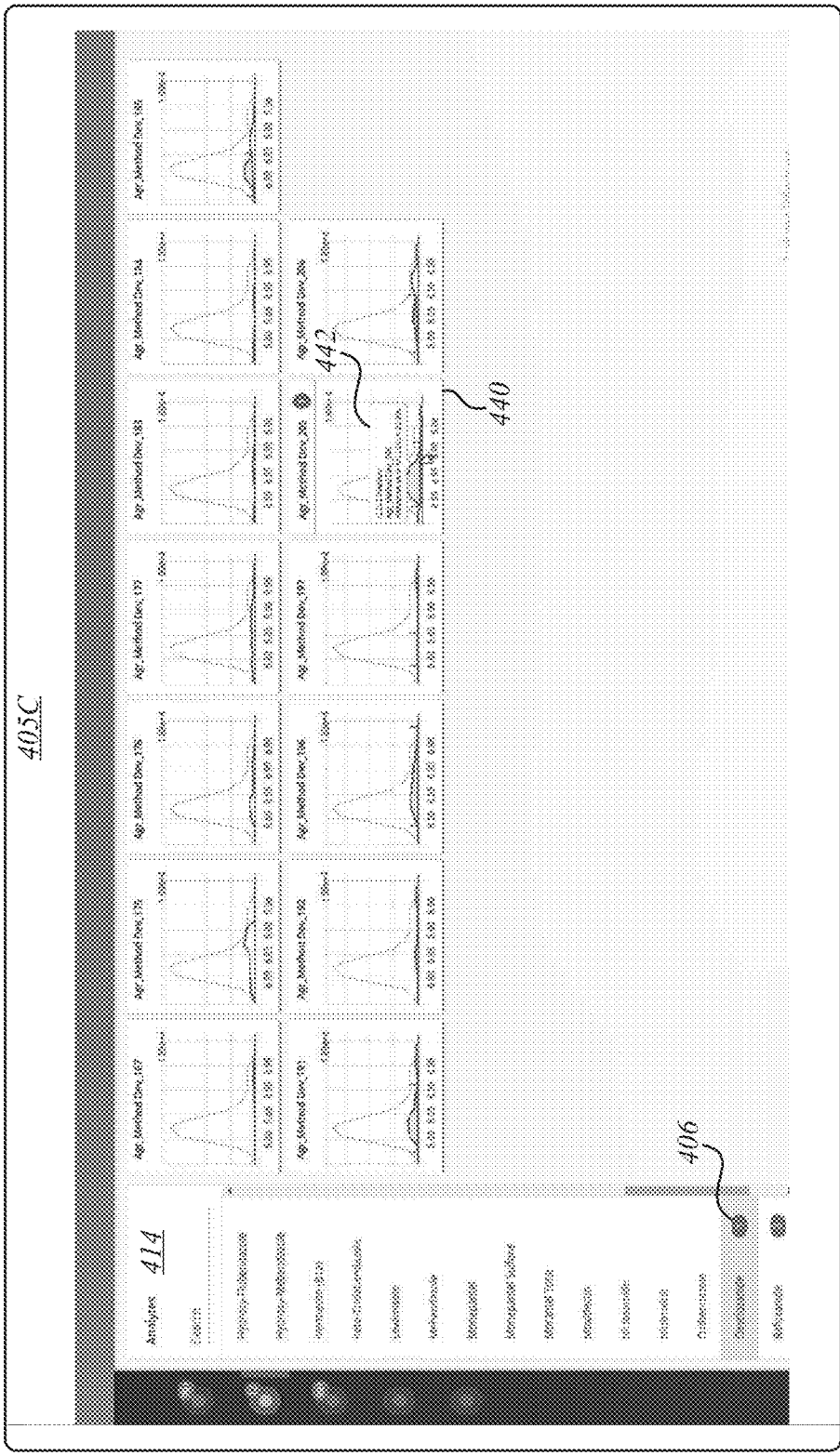

FIGS. 4A-4C illustrate an example of an operating environment 400 that may be representative of some embodiments. As shown in FIGS. 4A-4C, operating environment 400 may present information assessment screens 405A-C in the form of a blanks screen. For example, blanks screen 405A may depict a plot 402 and curve 410 for a particular blank analyte. In various embodiments, blanks screen 405 may present a blanks analytes listing 414, which may include an exception indicator 404 for any blank analyte associated with an exception. Accordingly, a user may browse through a listing of analytes and view blank assessment objects (for instance, plots, curves, and/or the like) associated with a particular analyte, including, for example, analytes associated with an exception.

Referring to FIG. 4B, information assessment processes according to some embodiments may allow a user to compare what is shown in the blank with a LLOQ (for example, which may indicate contamination, carryover, etc.). For example, a blank curve 402 may include an LLOQ plot or curve 414 (for example, as a background or "ghosted" peak), which may be associated with LLOQ information 430. In some embodiments, the LLOQ information may be configured by a user.

In some embodiments, an exception may be generated if the integrated region in a blank gets more than a threshold percentage (for example, 20%) of an LLOQ plot. Referring to FIG. 4C, therein is depicted a blanks screen 405C presented responsive to selection of the "Oxyclozanide" analyte from analyte list, associated with exception indicator 406. Selection of plot 440 or components thereof may cause presentation of LLOQ information, for example, indicating that the blank is out of range (for instance, response as a percentage of LLOQ is 23.9%, which is out of range for a 20% threshold). In various embodiments, selection of plot 440 or components thereof may cause the presentation of an exception management screen or other object to allow a user to manage the exception (for instance, flagging the exception, changing LLOQ parameters, selecting to ignore the exception, combinations thereof, and/or the like). In various embodiments, a user may select to only view analytes with an exception. For example, an exception toggle GUI object may limit analyte list 414 to only list analytes and/or present active selections (for instance, gray-out non-exception analytes) for analytes associated with an exception.

Figure 5A:
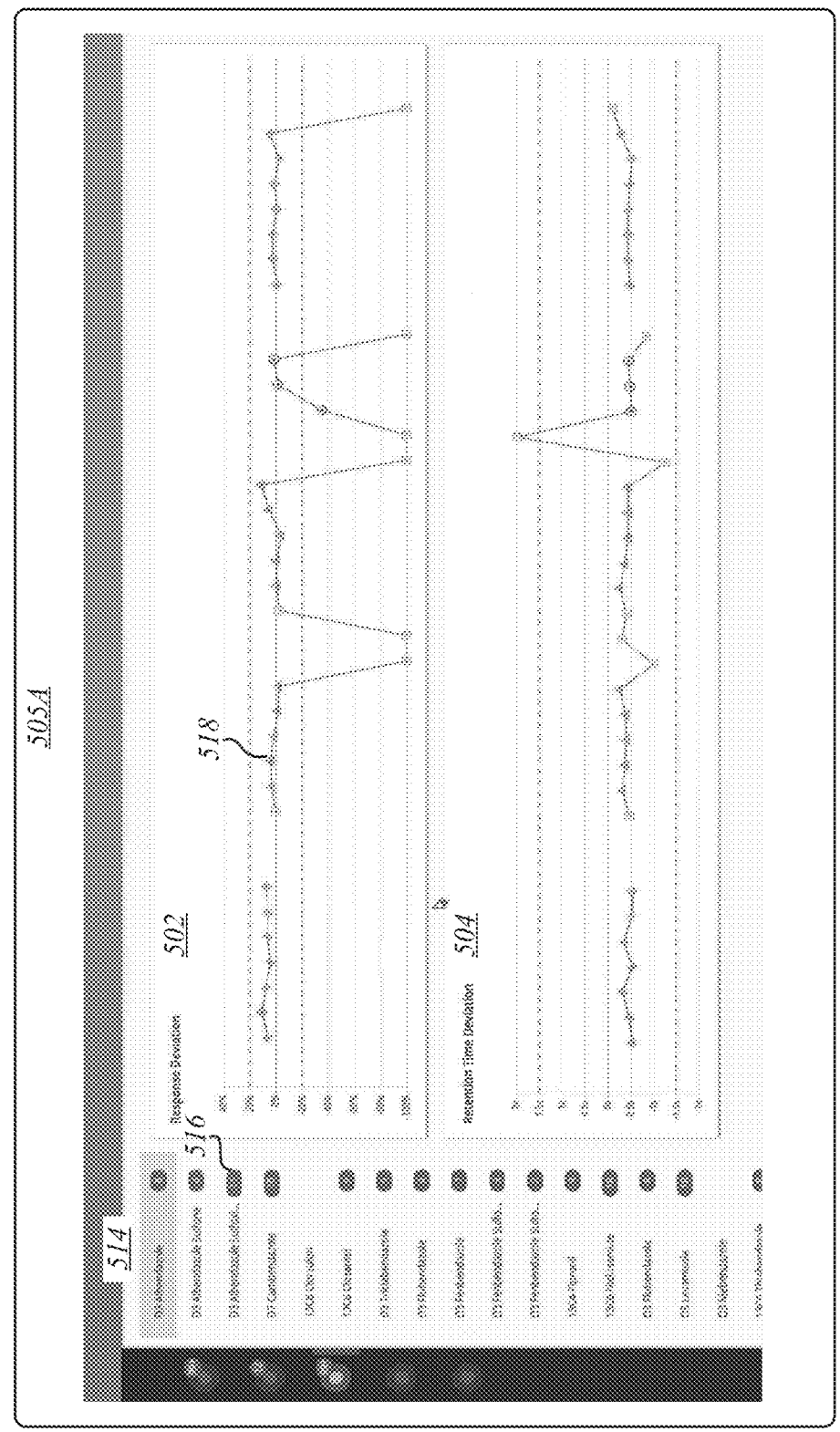
FIGS. 5A-5D illustrate an embodiment of a fifth operating environment.

FIGS. 5A-5D illustrate an example of an operating environment 500 that may be representative of some embodiments. As shown in FIGS. 5A-5D, operating environment 500 may present information assessment screens 505A-D in the form of standards or internal standards screens. Referring to FIG. 5A, internal standard screen 505A may include an analyte list 514 listing analytes, for example, associated with selected analytical information and any associated exception indicators 516. In various embodiments, internal standard screen 505A may present a response deviation plot 502 and/or a retention time deviation plot 504 for a selected internal standard (for instance, D3 Albendazole for FIG. 5A).

Figure 5B:
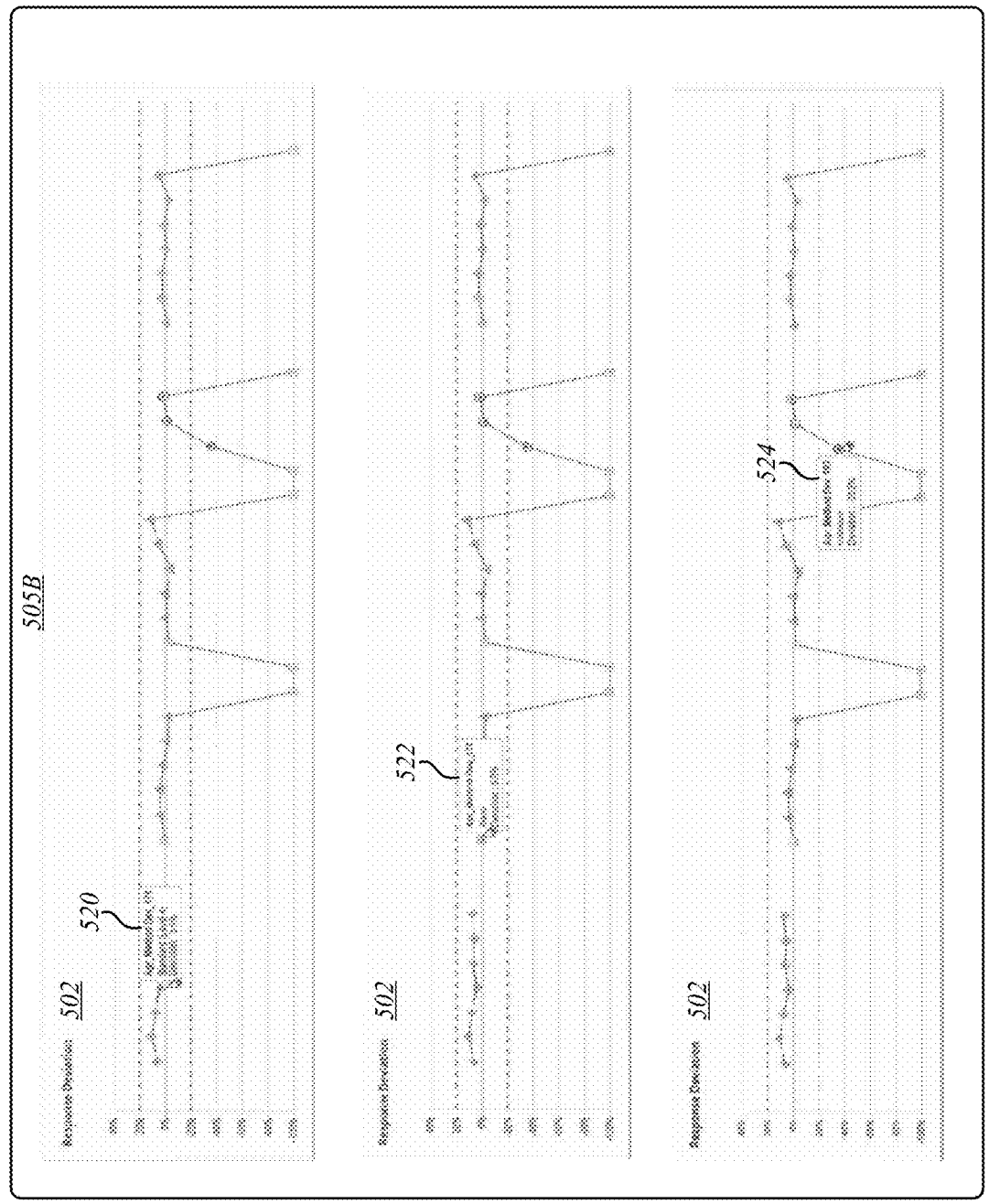

In exemplary embodiments, data points 518 may have various presentation characteristics to indicate certain information, such as the type of data point (for example, blank, internal standard, QCs, samples or unknowns, and/or the like), exceptions, and/or the like. Accordingly, a user may be able to efficiently visualize which category of analyte, QC, etc. may be associated with an exception. In some embodiments, plots 502, 504 may include threshold information (dashed lines) operative to indicate thresholds associated with the displayed analytical information, for example, that may be used as a basis for determining exceptions. As depicted in FIG. 5B, selection of a data point may cause presentation of a data point information object 520, 522, and 524 with data point information, such as data file information, data processing method information, type of data point, deviation percentage, and/or the like.

Figure 5C:
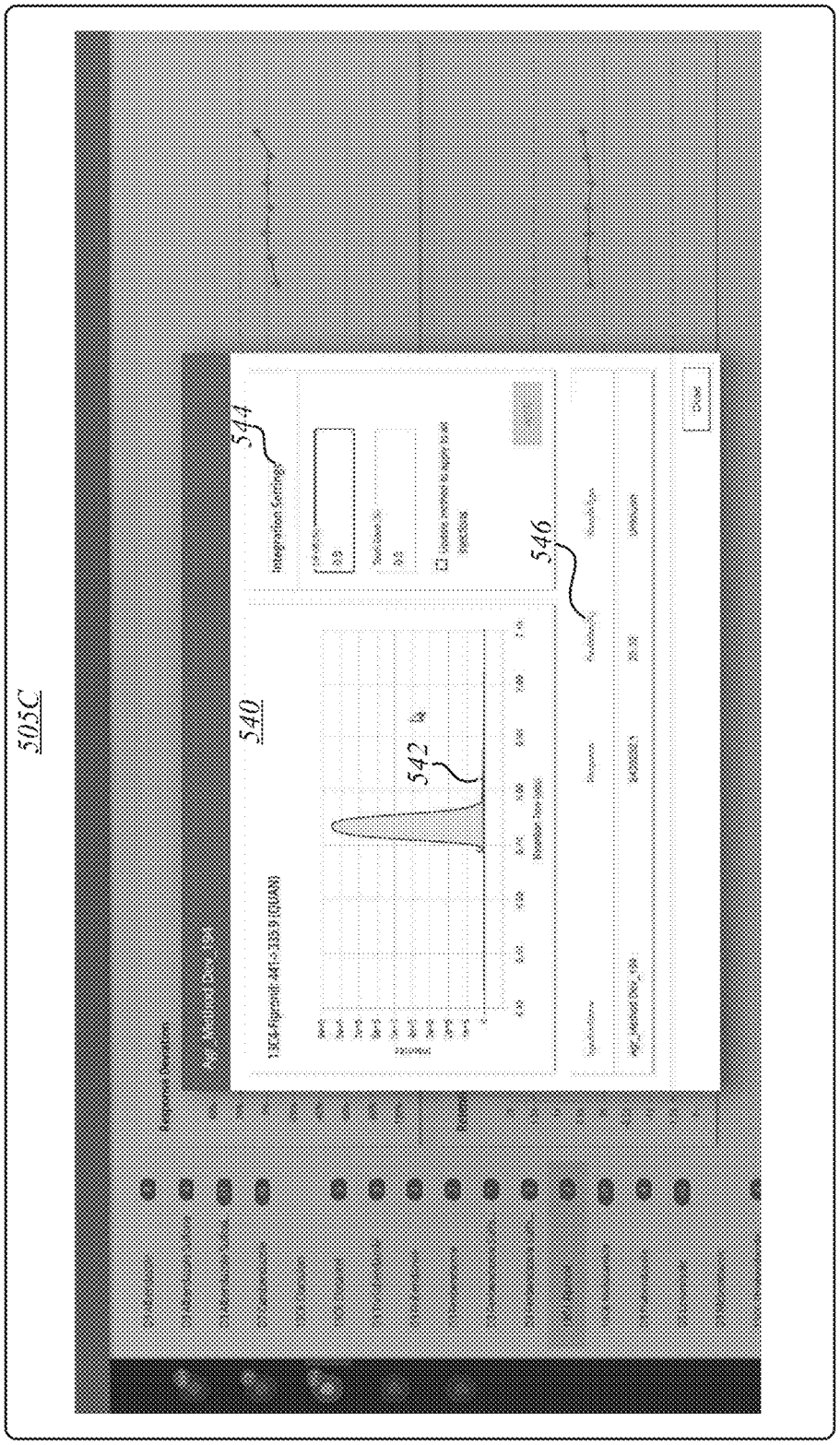
Figure 5D:
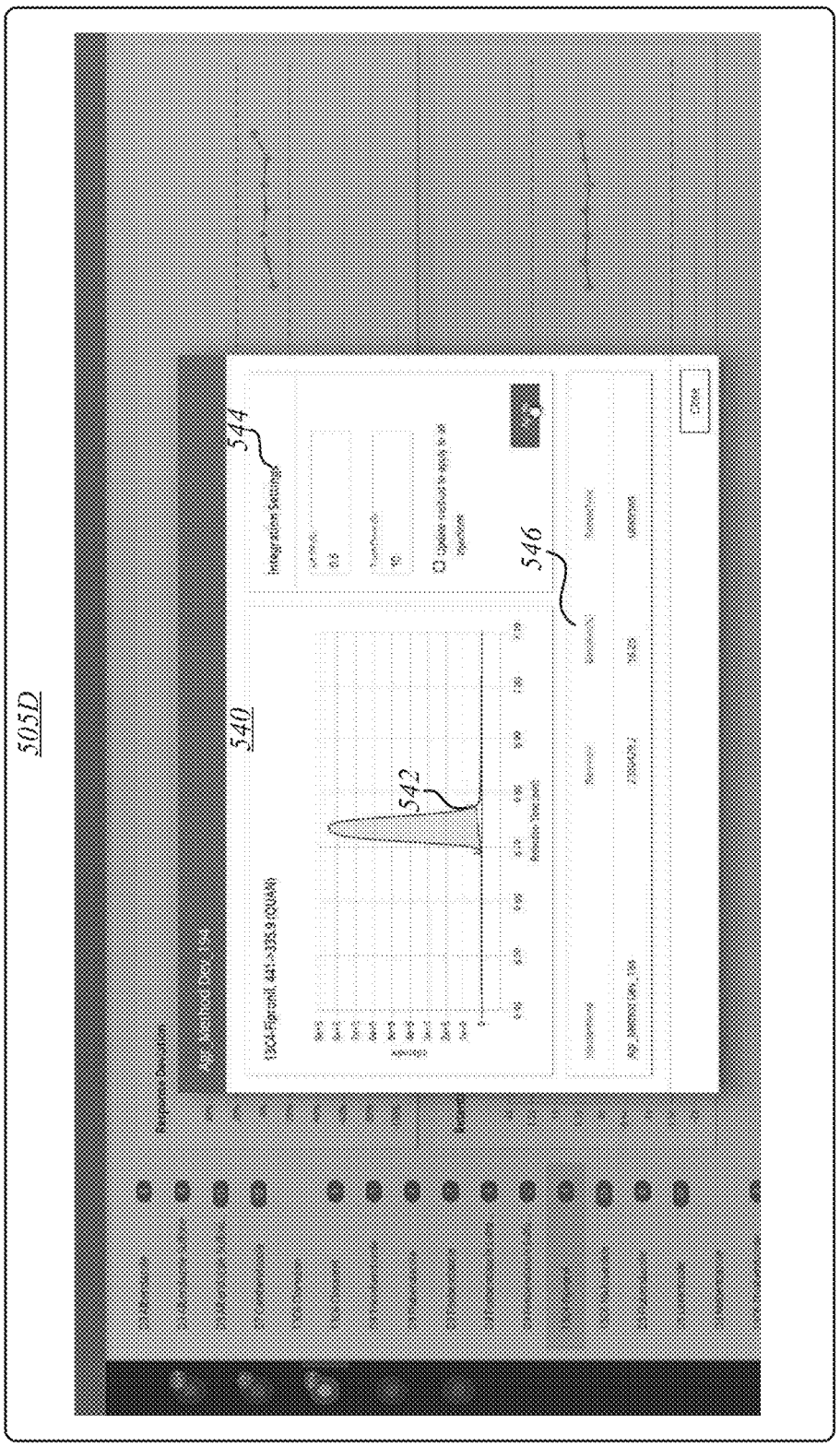

In some embodiments, information assessment processes may operate to facilitate addressing exceptions via internal standards screen 505A-D. Referring to FIG. 5C, selection of a data point having an exception may cause presentation of a chromatogram screen or window 540 showing an integration object 542, integration settings 544, and data point information 546, such as a deviation percentage. A user may modify one or more of integration settings 544, for example, as depicted in FIG. 5C, the "Touch Down (%)" value has been changed to 10, causing a change in integration object 542 and, therefore, deviation percentage (which is now below the threshold value of 20%).

Figure 6A:
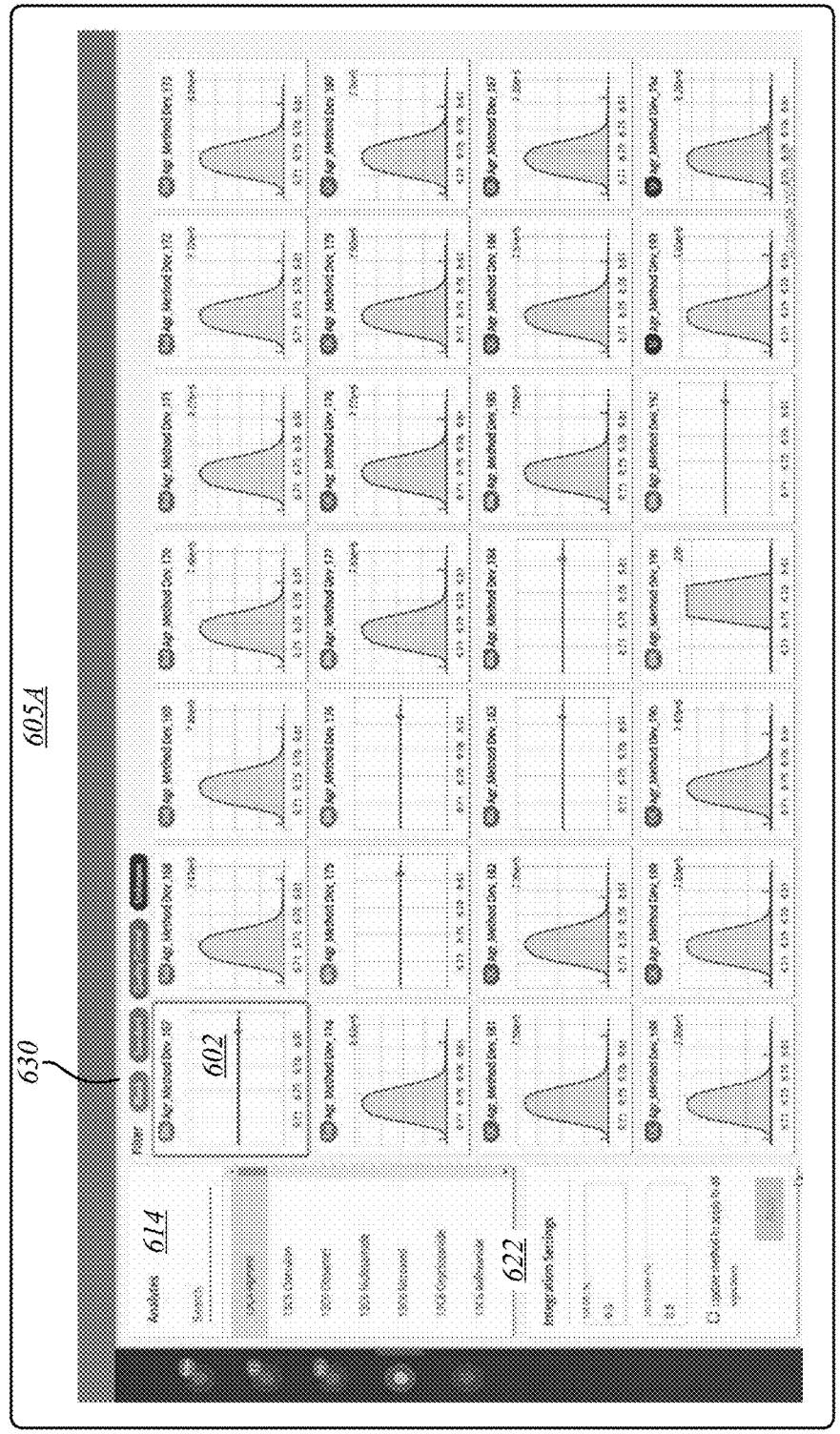
FIGS. 6A-6C illustrate an embodiment of a sixth operating environment.
Figure 6B:
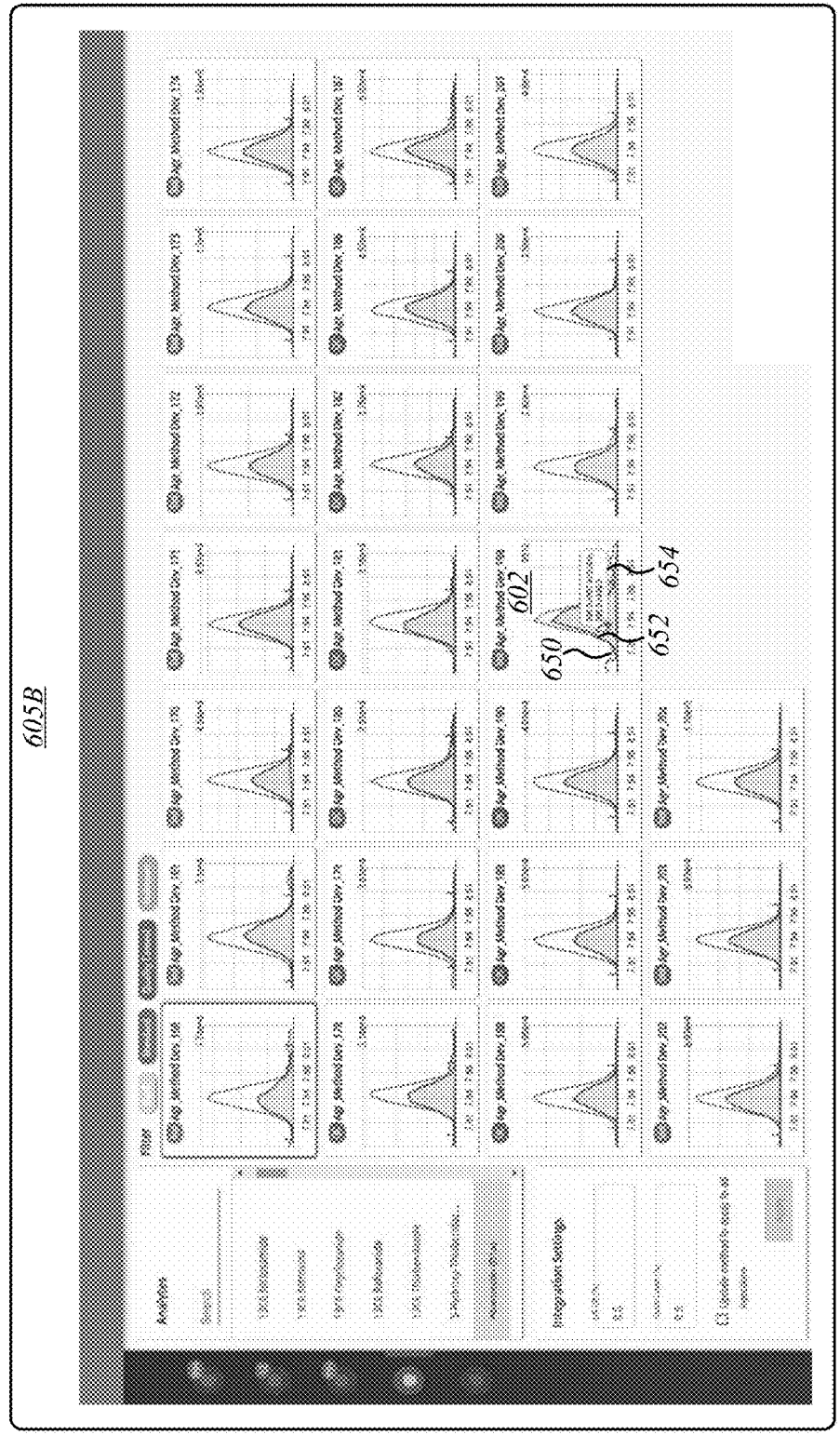
Figure 6C:
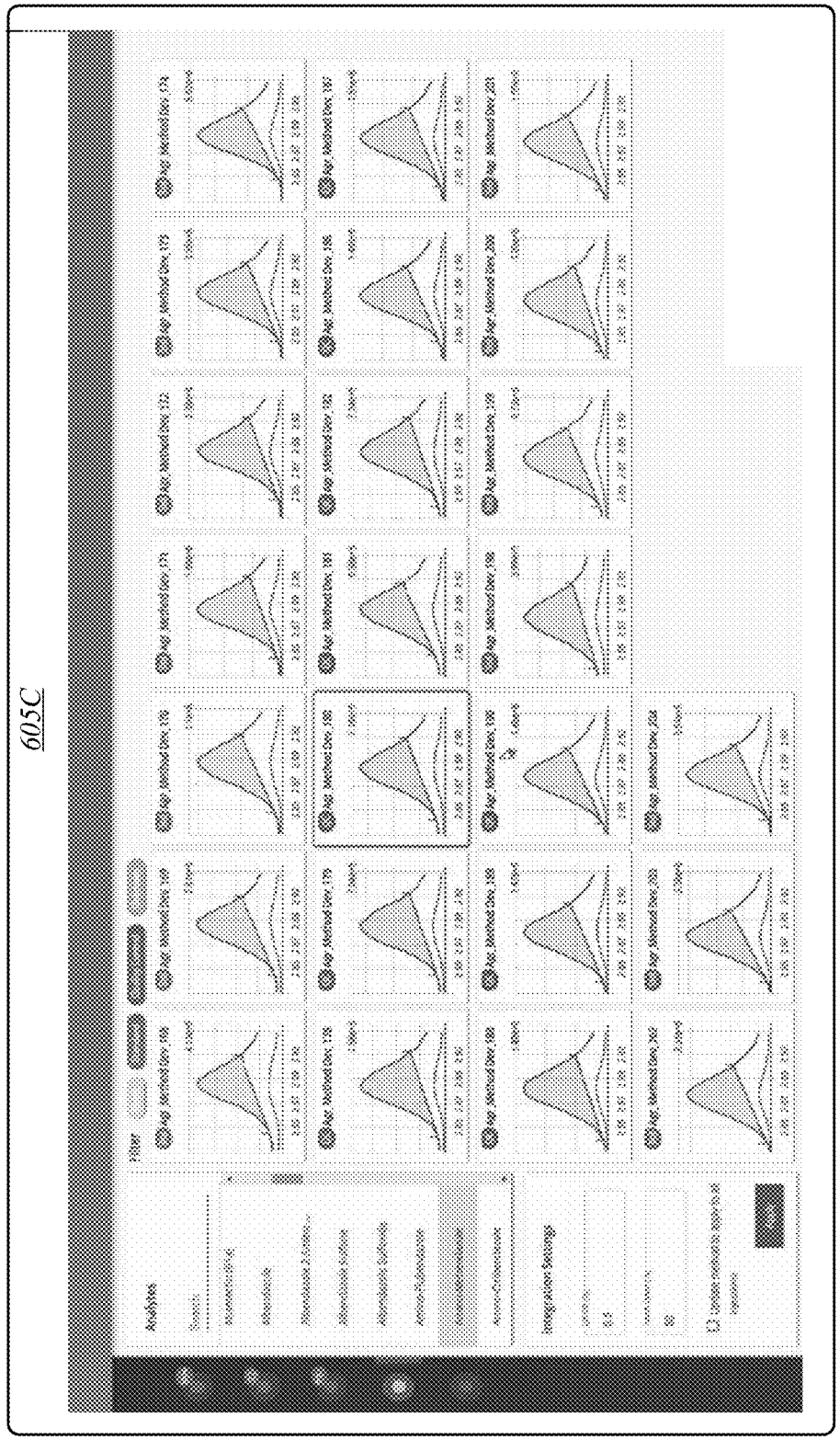

FIGS. 6A-6C illustrate an example of an operating environment 600 that may be representative of some embodiments. As shown in FIGS. 6A-6C, operating environment 600 may present information assessment screens 605A-C in the form of integration or peak integration screens. Referring to FIG. 6A, peak integration screen 605A may include an analyte listing 614 and integration settings for a selected analyte. Integration plots 602 may be presented for various types of analytes, such as blanks, standards, QCs, samples or unknowns, and/or the like. In some embodiments, a filter 630 may operate to filter display of integration plots for selected types of analytes (for example, a user may select filter 630 to only display integration plots 602 for blanks). In various embodiments, a user may select to only display integration plots 602 associated with exceptions (for example, abnormal/unexpected ion ratio, abnormal peak shapes, peak shapes outside of tolerance, and/or the like). In exemplary embodiments, peak integration screen 605A may depict integration plots 602 with the same or substantially the same Y-axis and/or X-axis, for example, to facilitate comparison and/or assessment of peak integrations.

Referring to FIG. 6B, peak integration screen 605B for an analyte (for example, Abamectin (B1a)). For example, integration plot 602 may depict a quantification (or qualification) trace 650 and an analyte or actual plot or trace 652. Selection of integration plot 602 and/or a portion thereof may depict plot information associated with quantification trace 650 and/or analyte plot 652. In some embodiments, a deviation between quantification trace 650 and analyte plot 652 over a threshold amount may trigger an exception, for example, an ion ratio exception. In some embodiments, a user may use integration settings 622 to attempt to address any exceptions. For example, referring to FIG. 6C, peak integration screen 605C depicts plots 602 where the "Touch Down (%)" integration setting 622 has been set to 80 and applied to all plots. Accordingly, in some embodiments, an x-axes for a plurality of plots may be set or resent depending on modified integration and/or injection settings.

As discussed in the present disclosure, conventional peak processing technologies have multiple inefficiencies and other limitations. For example, conventional integration algorithms are unable to provide accurate, useful error indicators or levels of confidence on measured peak attributes. Accordingly, information assessment processes, including review-by-exception, may use thresholds such that whether a peak has been measured accurately or not may not play a direct role in review-by-exception. In another example, integration results can be very sensitive to noise. As a result, for instance, rather than obtaining a similar result to one obtained with more noisy data, but with less confidence, the result could be radically altered as the peak baseline may have been poorly placed. According, some embodiments may use a probability-based analysis process to implement review-by-exception according to various embodiments.

Figure 7A:
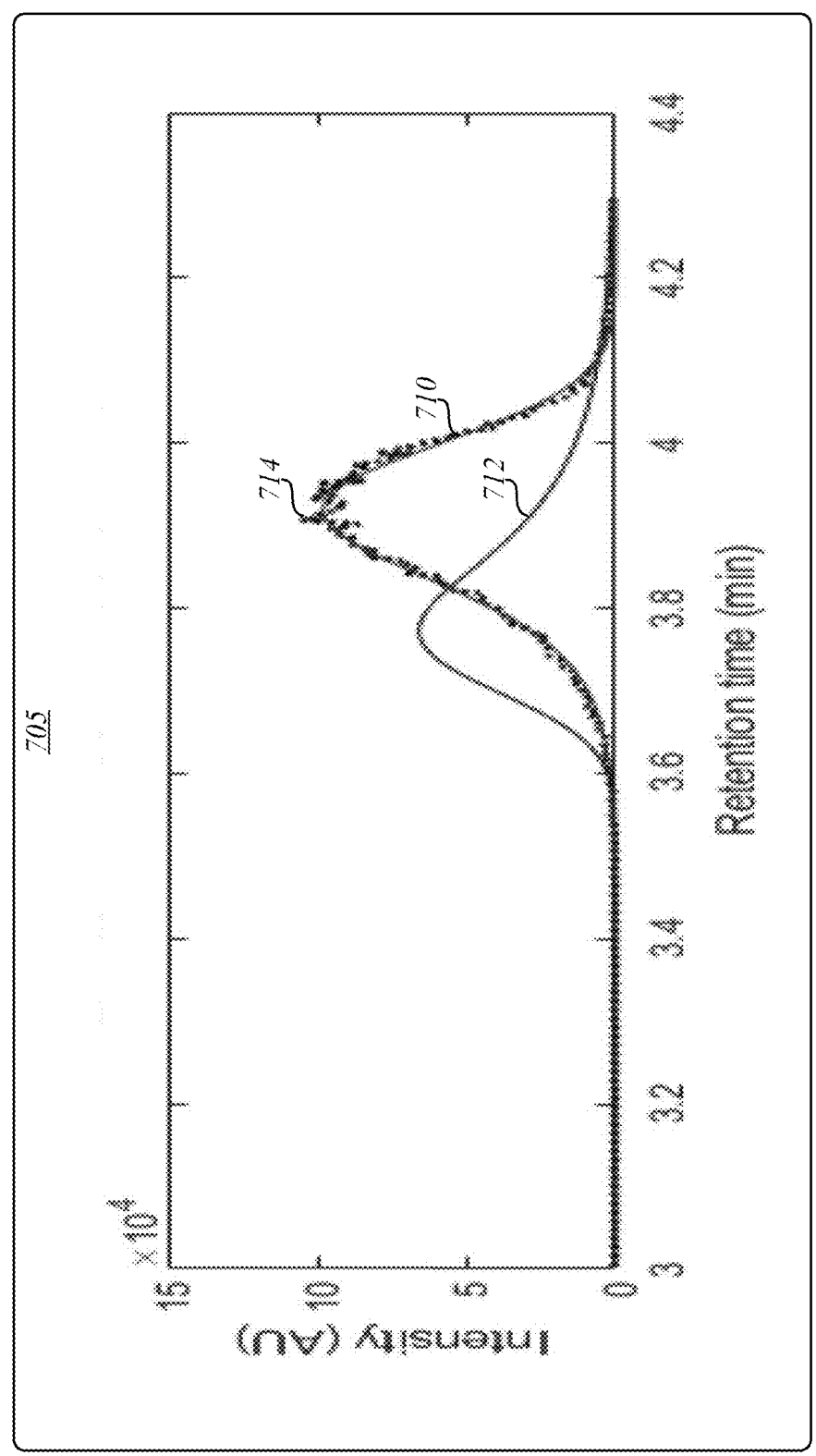
FIGS. 7A-7E illustrate embodiments of a seventh operating environment.

In some embodiments, a probability-based analysis process may use a Bayesian probabilistic analysis of analysis information, such as chromatographic data. For example, in order to extract meaningful measurements out of raw data, Bayesian data analysis may use probability concepts to derive an expression for the (posterior) probability that some theoretical model is the correct explanation of the chromatographic data. For instance, a theoretical model often used in chromatography, such as exponentially modified Gaussian peak may be used according to some embodiments. FIG. 7A depicts analytical information associated with different models. As shown in FIG. 7A, graph 705 shows raw MRM chromatogram with two different exponentially modified Gaussian peaks 710 and 712 based on different models. The models have one or more different characteristics, including, without limitation, positions, quantities, peak widths, and/or peak tailing values. In general, Bayesian theory may allow for an expression for the probability that one of a plurality of different models are the correct (or most correct or optimum) explanation of the data given a specific set of data. Although MRM and/or chromatogram information are used as examples in the present disclosure, embodiments are not so limited. For example, the processes described according to some embodiments, including review-by-exception processes, probability-based analysis processes, and/or the like may be applied to various different types of data.

As indicated by FIG. 7A, one of the models has a much higher probability of being the correct explanation of the data than the other (i.e., model 710, which more closely follows the data plots 714). Accordingly, there may be a multitude of potential models, each with some associated (posterior) probability. A total probability for the models, which must sum to one, is shared between all potential models, leading to a probability distribution over the set of peak parameters. For a given model, the posterior probability may depend on how well the model matches the data, which may be referred to as the likelihood or the probability of the data given the model (not to be confused with the probability of the model given the data). In addition, in some embodiments, information that is already know may also be a fundamental input to the process and, for example, may be expressed as a "prior probability." For instance, referring to graph 705, there is zero probability of there being a peak at 3 minutes.

Accordingly, in some embodiments, a probability-based analysis process may use an underlying probability distribution to extract meaningful measurements from the data and to determine a level of confidence in those measurements. In various embodiments, the extraction of meaningful measurements and/or determination of an associated level of confidence may be based on, among other things, by determining and/or evaluating samples from a probability distribution. In some embodiments, the samples may be determined and/or evaluated using Markov chain Monte Carlo (MCMC) and/or nested sampling, for example, the same or similar to the method described in Skilling, "Nested Sampling for General Bayesian Computation," Bayesian Analysis, No. 4, pp. 833-860 (2006). For instance, for chromatographic data, some embodiments may implement chromatographic peak detection and integration using nested sampling and/or Markov chain Monte Carlo.

In general, Markov chain Monte Carlo is a computation technique using random numbers to generate samples from an unknown probability distribution. Nested sampling uses Markov chain Monte Carlo to obtain (for example, weighted) samples from a posterior distribution. For example, some embodiments may use repeated samples or measurements of peak position, width, asymmetry and quantity in accordance with a probability that the given sample (for instance, peak model) is the correct (or most correct or optimal) explanation of the data (for instance, once the weightings have been allowed for).

Figure 7B:
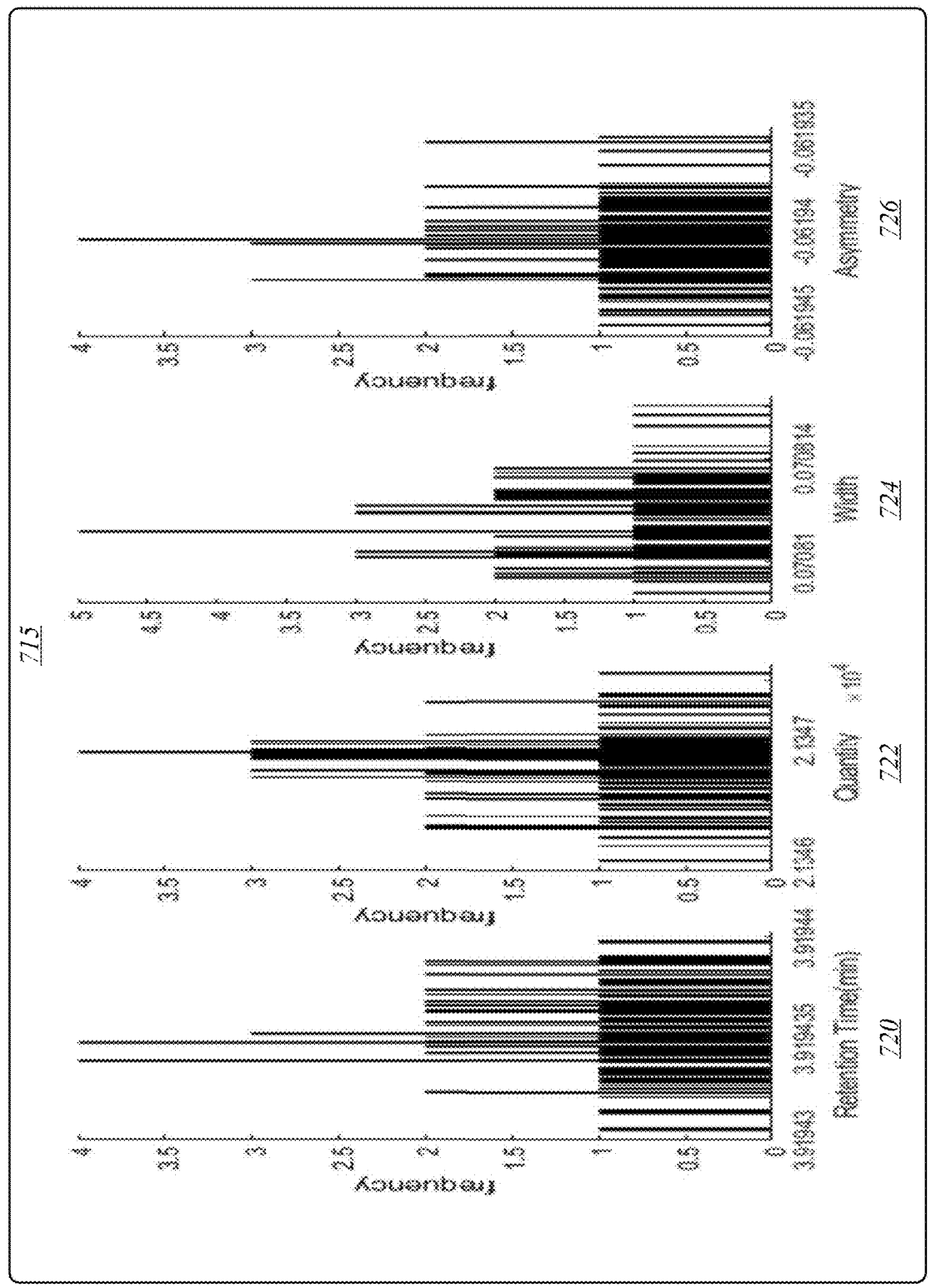

FIG. 7B depicts posterior probability samples of analytical information. Referring to FIG. 7B, therein is depicted graph 715 of posterior probability values of chromatographic information over the peak attributes of retention time 720, quantity 722, width 724, and asymmetry 726. In various embodiments, the distribution values may be used to provide an estimate of each of the peak attributes along with error bars for those estimates.

The posterior samples may represent what is known about the presence of a peak in the data, along with the attributes of that peak. In some embodiments, the probability-based analysis process may be general and may allow multiple peaks to be discovered. In other embodiments, the probability-based analysis process may involve a "targeted" approach or application involving expected information (for example, expected information as part of prior input, such as the presence of a single eluting compound (i.e., peak)).

In some embodiments, with a targeted approach, it may be relatively straight forward to summarise the data by taking the mean of the samples for each of the attributes being sampled. Such estimates may provide an accepted peak model as an explanation of the data. However, there may be in effect multiple peak measurements and it is the spread or dispersion of these measurements that may provide some indication of the accuracy of those measurements.

Figure 7C:
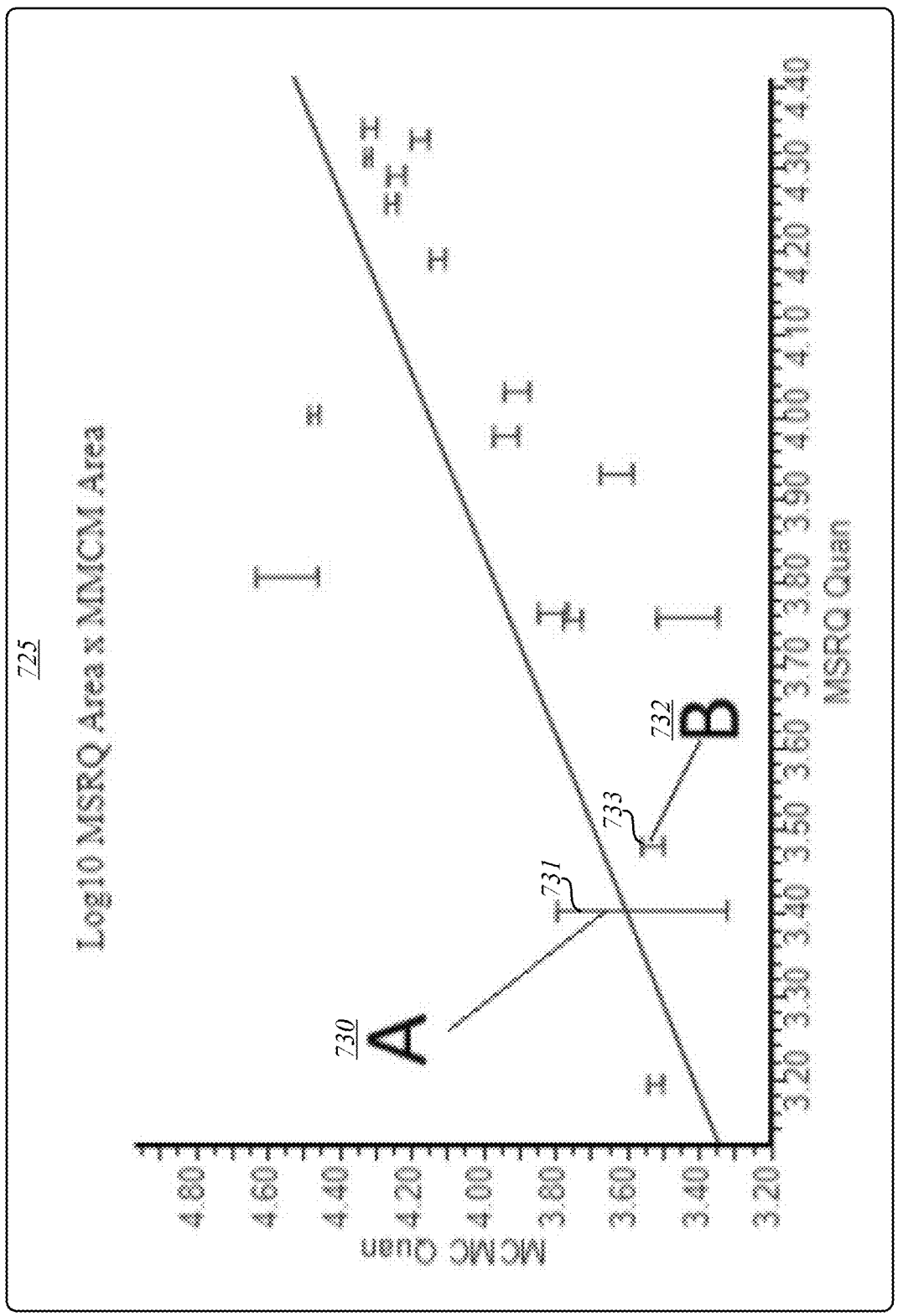

In some embodiments, standard error of the mean (or other process for determining error, standard deviation, and/or the like) may be used to provide error bars, for example, to provide an indication of the accuracy of associated measurements. FIG. 7C depicts a graph of analytical information with measurements associated with error bars configured according to some embodiments. Referring to FIG. 7C, graph 725 depicts area results for multiple compounds obtained using certain quantification/integration techniques (MSRQ Quan axis) against results obtained via probability-based analysis processes according to some embodiments (MCMC Quan axis). In FIG. 7C, the MCMC results are associated with error bars (adjusted for logarithmic axis), for example, measurement A 730 and measurement B 732.

As shown in FIG. 7, the error (error bar, divergence, uncertainty, and/or the like) associated with measurement A 730 as indicated by the associated error bar 731 compared to the error bar 733 associated with measurement B 732 provides results that display widely different levels of uncertainty. Accordingly, in some embodiments, measurement A 730 may be flagged as an exception for review in a review-by-exception process, while measurement B 732 may not be flagged as an exception. In various embodiments, the error, error bar, uncertainty, or "confidence indicator" may be compared with an exception threshold. If the confidence indicator is over (or under, depending on the value scheme) or otherwise outside of the exception threshold, then the measurement (or peak) may be flagged as an exception.

Figure 7D:
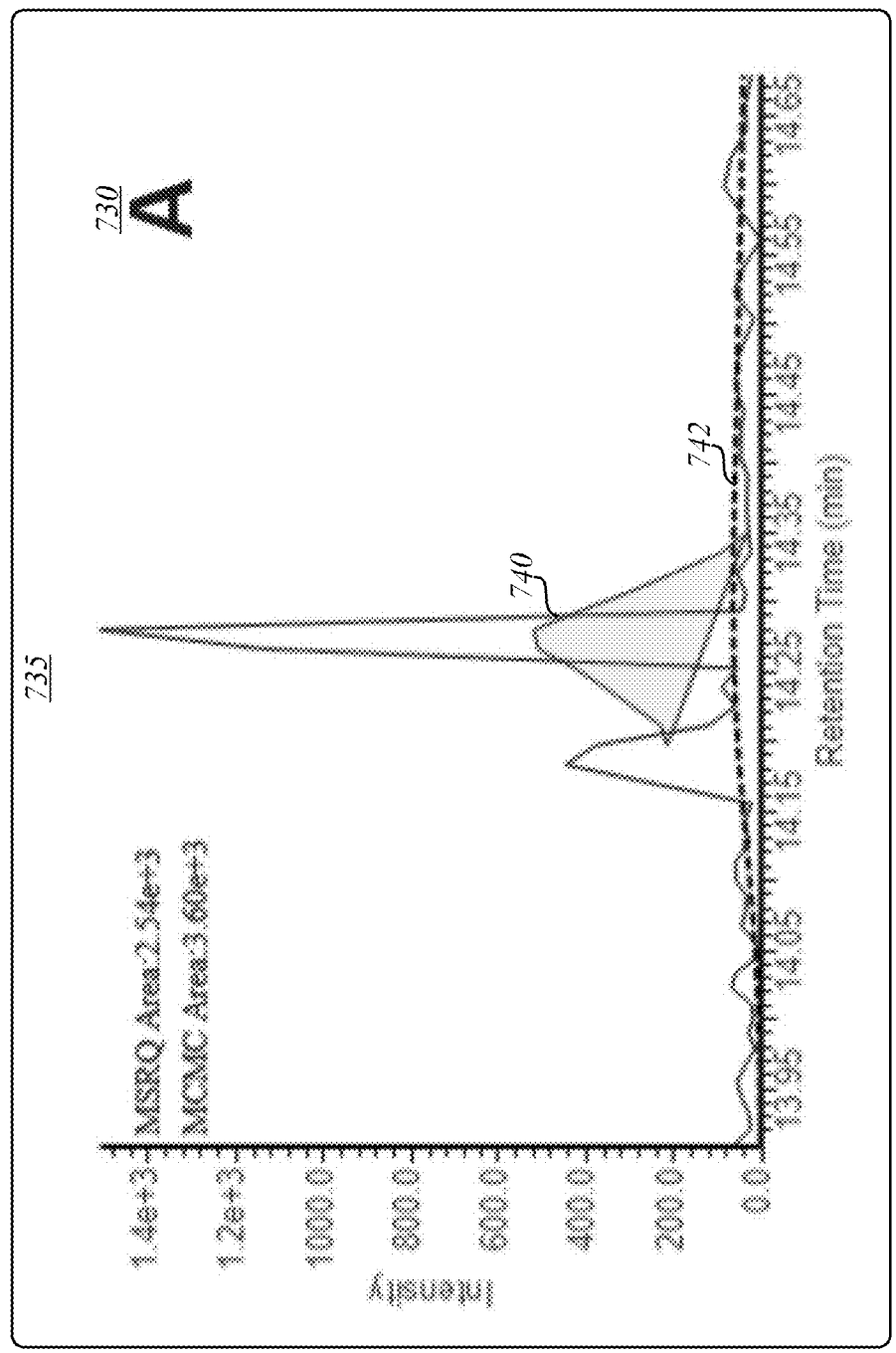
Figure 7E:
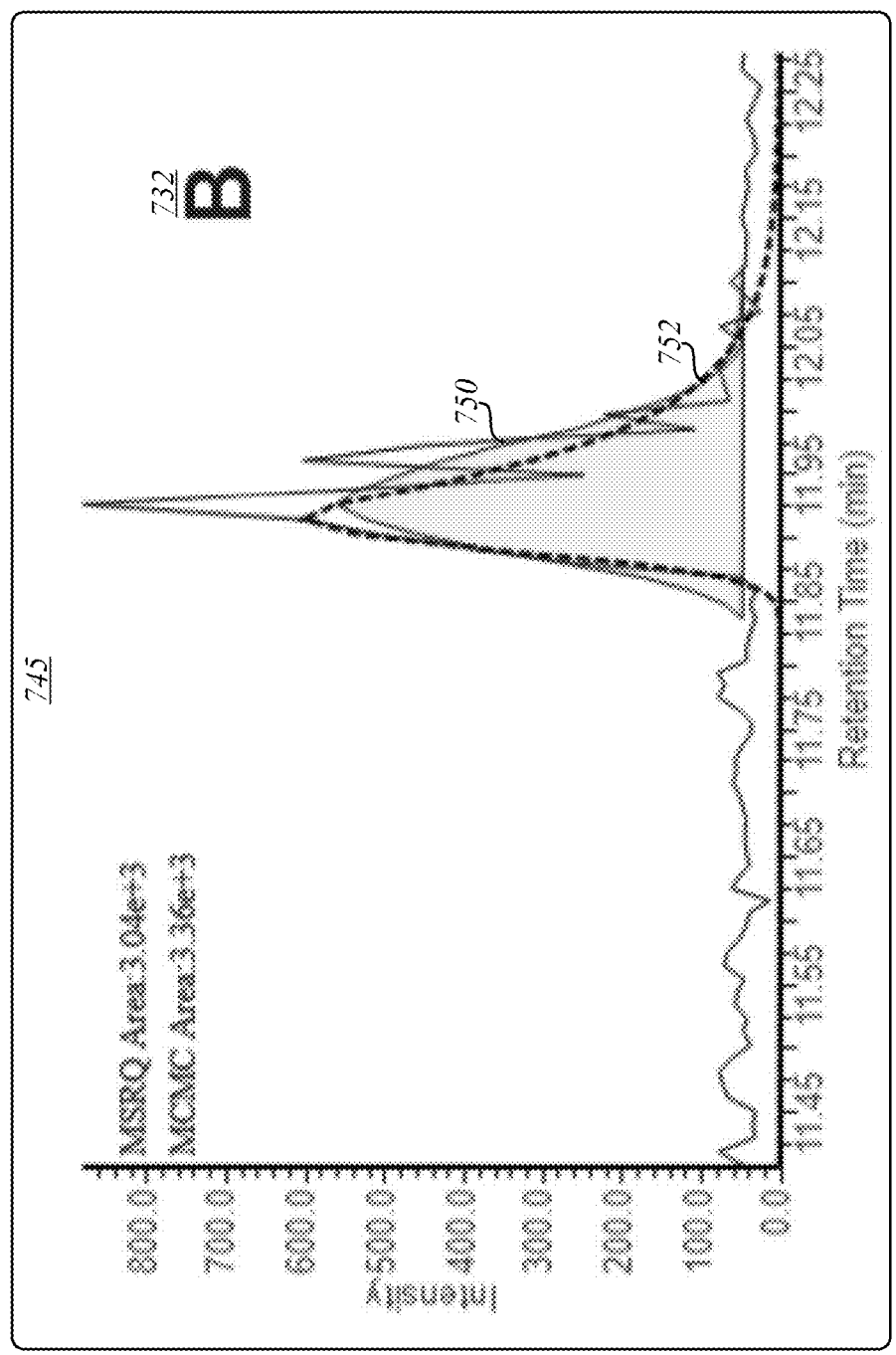

FIG. 7D depicts integration results corresponding to measurement A of FIG. 7C and FIG. 7E depicts integration results corresponding to measurement B of FIG. 7C. Referring to FIG. 7D, therein is illustrated a graph 735 showing an estimated peak model 740 and a conventional result 742 (e.g., filled peak) corresponding to measurement A 730 (i.e., area of 3.60e+3 versus 2.54e+3). In FIG. 7E, therein is depicted a graph 745 showing an estimated peak model 750 and a conventional result 752 (e.g., filled peak) corresponding to measurement B 732 (i.e., area of 3.36e+3 versus 3.04e+3). In some embodiments, the difference between the MCMC value (i.e., a probability-based value) and the MSRQ value (conventional quantification/integration method value) may be used as the confidence indicator (for example, as a probability-conventional difference value). Referring to FIGS. 7D and 7E, the confidence indicator ((probability-based value)−(conventional value) or a ratio of the probability-based value and the conventional value) of graph 735 may be sufficient to raise an exception, while the confidence indicator of graph 745 may not be sufficient to raise an exception (i.e., there is a sufficient level of confidence in measurement B 732).

In various embodiments, error bars and/or probability-conventional difference (or other relationship, such as a ratio) may be used to generate a confidence indicator indicating a confidence (or, conversely, uncertainty) in the data. In various embodiments, a review-by-exception process may include one or more thresholds for flagging results for review based on the confidence factor (for example, a probability-conventional difference (or ratio) greater than X may be flagged as an exception requiring review). Embodiments are not limited in this context.

Figure 8:
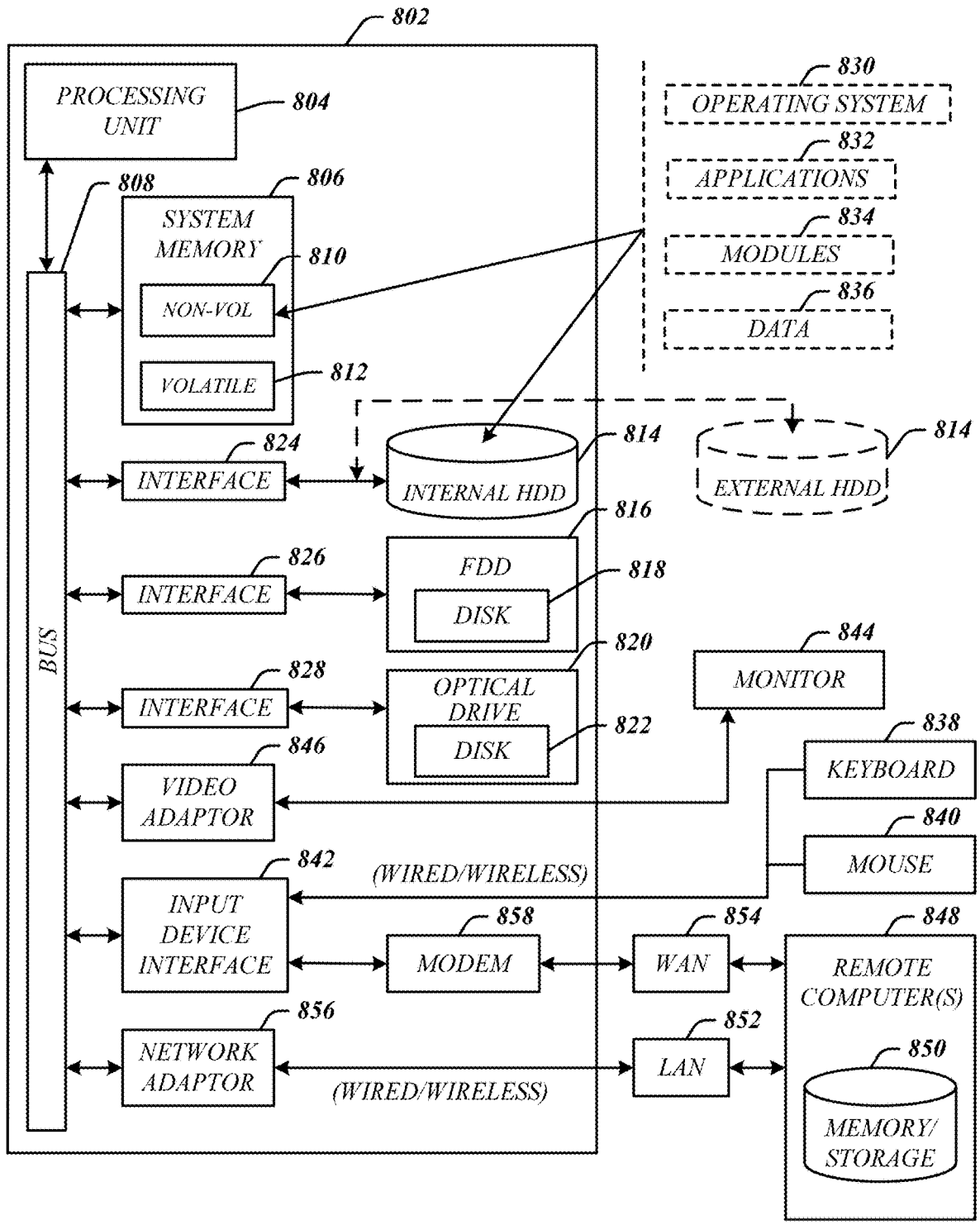
FIG. 8 illustrates an embodiment of a computing architecture.

FIG. 8 illustrates an embodiment of an exemplary computing architecture 800 suitable for implementing various embodiments as previously described. In various embodiments, the computing architecture 800 may comprise or be implemented as part of an electronic device. In some embodiments, the computing architecture 800 may be representative, for example, of computing device 110. The embodiments are not limited in this context.

As used in this application, the terms "system" and "component" and "module" are intended to refer to a computer-related entity, either hardware, a combination of hardware and software, software, or software in execution, examples of which are provided by the exemplary computing architecture 800. For example, a component can be, but is not limited to being, a process running on a processor, a processor, a hard disk drive, multiple storage drives (of optical and/or magnetic storage medium), an object, an executable, a thread of execution, a program, and/or a computer. By way of illustration, both an application running on a server and the server can be a component. One or more components can reside within a process and/or thread of execution, and a component can be localized on one computer and/or distributed between two or more computers. Further, components may be communicatively coupled to each other by various types of communications media to coordinate operations. The coordination may involve the uni-directional or bi-directional exchange of information. For instance, the components may communicate information in the form of signals communicated over the communications media. The information can be implemented as signals allocated to various signal lines. In such allocations, each message is a signal. Further embodiments, however, may alternatively employ data messages. Such data messages may be sent across various connections. Exemplary connections include parallel interfaces, serial interfaces, and bus interfaces.

The computing architecture 800 includes various common computing elements, such as one or more processors, multi-core processors, co-processors, memory units, chipsets, controllers, peripherals, interfaces, oscillators, timing devices, video cards, audio cards, multimedia input/output (I/O) components, power supplies, and so forth. The embodiments, however, are not limited to implementation by the computing architecture 800.

As shown in FIG. 8, the computing architecture 800 comprises a processing unit 804, a system memory 806 and a system bus 808. The processing unit 804 can be any of various commercially available processors, including without limitation an AMD® Athlon®, Duron® and Opteron® processors; ARM® application, embedded and secure processors; IBM® and Motorola® DragonBall® and PowerPC® processors; IBM and Sony® Cell processors; Intel® Celeron®, Core (2) Duo®, Itanium®, Pentium®, Xeon®, and XScale® processors; and similar processors. Dual microprocessors, multi-core processors, and other multi-processor architectures may also be employed as the processing unit 804.

The system bus 808 provides an interface for system components including, but not limited to, the system memory 806 to the processing unit 804. The system bus 808 can be any of several types of bus structure that may further interconnect to a memory bus (with or without a memory controller), a peripheral bus, and a local bus using any of a variety of commercially available bus architectures. Interface adapters may connect to the system bus 808 via a slot architecture. Example slot architectures may include without limitation Accelerated Graphics Port (AGP), Card Bus, (Extended) Industry Standard Architecture ((E)ISA), Micro Channel Architecture (MCA), NuBus, Peripheral Component Interconnect (Extended) (PCI(X)), PCI Express, Personal Computer Memory Card International Association (PCMCIA), and the like.

The system memory 806 may include various types of computer-readable storage media in the form of one or more higher speed memory units, such as read-only memory (ROM), random-access memory (RAM), dynamic RAM (DRAM), Double-Data-Rate DRAM (DDRAM), synchronous DRAM (SDRAM), static RAM (SRAM), programmable ROM (PROM), erasable programmable ROM (EPROM), electrically erasable programmable ROM (EEPROM), flash memory, polymer memory such as ferroelectric polymer memory, ovonic memory, phase change or ferroelectric memory, silicon-oxide-nitride-oxide-silicon (SONOS) memory, magnetic or optical cards, an array of devices such as Redundant Array of Independent Disks (RAID) drives, solid state memory devices (e.g., USB memory, solid state drives (SSD) and any other type of storage media suitable for storing information. In the illustrated embodiment shown in FIG. 8, the system memory 806 can include non-volatile memory 810 and/or volatile memory 812. A basic input/output system (BIOS) can be stored in the non-volatile memory 810.

The computer 802 may include various types of computer-readable storage media in the form of one or more lower speed memory units, including an internal (or external) hard disk drive (HDD) 814, a magnetic floppy disk drive (FDD) 816 to read from or write to a removable magnetic disk 818, and an optical disk drive 820 to read from or write to a removable optical disk 822 (e.g., a CD-ROM or DVD). The HDD 814, FDD 816 and optical disk drive 820 can be connected to the system bus 808 by a HDD interface 824, an FDD interface 826 and an optical drive interface 820, respectively. The HDD interface 824 for external drive implementations can include at least one or both of Universal Serial Bus (USB) and IEEE 1384 interface technologies.

The drives and associated computer-readable media provide volatile and/or nonvolatile storage of data, data structures, computer-executable instructions, and so forth. For example, a number of program modules can be stored in the drives and memory units 810, 812, including an operating system 830, one or more application programs 832, other program modules 834, and program data 836. In one embodiment, the one or more application programs 832, other program modules 834, and program data 836 can include, for example, the various applications and/or components of computing device 110.

A user can enter commands and information into the computer 802 through one or more wire/wireless input devices, for example, a keyboard 838 and a pointing device, such as a mouse 840. Other input devices may include microphones, infra-red (IR) remote controls, radio-frequency (RF) remote controls, game pads, stylus pens, card readers, dongles, finger print readers, gloves, graphics tablets, joysticks, keyboards, retina readers, touch screens (e.g., capacitive, resistive, etc.), trackballs, trackpads, sensors, styluses, and the like. These and other input devices are often connected to the processing unit 804 through an input device interface 842 that is coupled to the system bus 808, but can be connected by other interfaces such as a parallel port, IEEE 1394 serial port, a game port, a USB port, an IR interface, and so forth.

A monitor 844 or other type of display device is also connected to the system bus 808 via an interface, such as a video adaptor 846. The monitor 844 may be internal or external to the computer 802. In addition to the monitor 844, a computer typically includes other peripheral output devices, such as speakers, printers, and so forth.

The computer 802 may operate in a networked environment using logical connections via wire and/or wireless communications to one or more remote computers, such as a remote computer 848. The remote computer 848 can be a workstation, a server computer, a router, a personal computer, portable computer, microprocessor-based entertainment appliance, a peer device or other common network node, and typically includes many or all of the elements described relative to the computer 802, although, for purposes of brevity, only a memory/storage device 850 is illustrated. The logical connections depicted include wire/wireless connectivity to a local area network (LAN) 852 and/or larger networks, for example, a wide area network (WAN) 854. Such LAN and WAN networking environments are commonplace in offices and companies, and facilitate enterprise-wide computer networks, such as intranets, all of which may connect to a global communications network, for example, the Internet.

When used in a LAN networking environment, the computer 802 is connected to the LAN 852 through a wire and/or wireless communication network interface or adaptor 856. The adaptor 856 can facilitate wire and/or wireless communications to the LAN 852, which may also include a wireless access point disposed thereon for communicating with the wireless functionality of the adaptor 856.

When used in a WAN networking environment, the computer 802 can include a modem 858, or is connected to a communications server on the WAN 854, or has other means for establishing communications over the WAN 854, such as by way of the Internet. The modem 858, which can be internal or external and a wire and/or wireless device, connects to the system bus 808 via the input device interface 842. In a networked environment, program modules depicted relative to the computer 802, or portions thereof, can be stored in the remote memory/storage device 850. It will be appreciated that the network connections shown are exemplary and other means of establishing a communications link between the computers can be used.

The computer 802 is operable to communicate with wire and wireless devices or entities using the IEEE 802 family of standards, such as wireless devices operatively disposed in wireless communication (e.g., IEEE 802.16 over-the-air modulation techniques). This includes at least Wi-Fi (or Wireless Fidelity), WiMax, and Bluetooth™ wireless technologies, among others. Thus, the communication can be a predefined structure as with a conventional network or simply an ad hoc communication between at least two devices. Wi-Fi networks use radio technologies called IEEE 802.11x (a, b, g, n, etc.) to provide secure, reliable, fast wireless connectivity. A Wi-Fi network can be used to connect computers to each other, to the Internet, and to wire networks (which use IEEE 802.3-related media and functions).

Numerous specific details have been set forth herein to provide a thorough understanding of the embodiments. It will be understood by those skilled in the art, however, that the embodiments may be practiced without these specific details. In other instances, well-known operations, components, and circuits have not been described in detail so as not to obscure the embodiments. It can be appreciated that the specific structural and functional details disclosed herein may be representative and do not necessarily limit the scope of the embodiments.

Some embodiments may be described using the expression "coupled" and "connected" along with their derivatives. These terms are not intended as synonyms for each other. For example, some embodiments may be described using the terms "connected" and/or "coupled" to indicate that two or more elements are in direct physical or electrical contact with each other. The term "coupled," however, may also mean that two or more elements are not in direct contact with each other, but yet still co-operate or interact with each other.

Unless specifically stated otherwise, it may be appreciated that terms such as "processing," "computing," "calculating," "determining," or the like, refer to the action and/or processes of a computer or computing system, or similar electronic computing device, that manipulates and/or transforms data represented as physical quantities (e.g., electronic) within the computing system's registers and/or memories into other data similarly represented as physical quantities within the computing system's memories, registers or other such information storage, transmission or display devices. The embodiments are not limited in this context.

It should be noted that the methods described herein do not have to be executed in the order described, or in any particular order. Moreover, various activities described with respect to the methods identified herein can be executed in serial or parallel fashion.

Although specific embodiments have been illustrated and described herein, it should be appreciated that any arrangement calculated to achieve the same purpose may be substituted for the specific embodiments shown. This disclosure is intended to cover any and all adaptations or variations of various embodiments. It is to be understood that the above description has been made in an illustrative fashion, and not a restrictive one. Combinations of the above embodiments, and other embodiments not specifically described herein will be apparent to those of skill in the art upon reviewing the above description. Thus, the scope of various embodiments includes any other applications in which the above compositions, structures, and methods are used.

Although the subject matter has been described in language specific to structural features and/or methodological acts, it is to be understood that the subject matter defined in the appended claims is not necessarily limited to the specific features or acts described above. Rather, the specific features and acts described above are disclosed as example forms of implementing the claims.

The invention claimed is:

1. An apparatus, comprising:
a memory;
one or more processors; and
instructions, stored in the memory and configured to be executed by the one or more processors to perform a review-by-exception process operative to:
access chromatography information generated via analyzing a sample using a mass spectrometry system, the chromatography information comprising at least one peak and at least one peak attribute for the at least one peak,
determine posterior probability information for the chromatography information,
generate an estimated peak model based on the posterior probability information,
determine a confidence indicator for the estimated peak model, and
generate an exception for the at least one peak responsive to the confidence indicator being outside of an exception threshold.

2. The apparatus of claim 1, the instructions, when executed by the one or more processors to perform a review-by-exception process, operative to generate at least one information assessment screen to present at least one graphical user interface (GUI) object to visually highlight the exception.

3. The apparatus of claim 1, the estimated peak model determined using Markov chain Monte Carlo and nested sampling.

4. The apparatus of claim 1, the posterior probability information generated via Bayesian probabilistic analysis.

5. The apparatus of claim 1, the posterior probability information comprising posterior probability samples for the at least one peak attribute, the at least one peak attribute comprising at least one of retention time, quantity, width, or asymmetry.

6. The apparatus of claim 1, the confidence indicator indicating a confidence that the estimated peak model models the chromatography information.

7. The apparatus of claim 1, the confidence indicator comprising at least one error bar.

8. A computer-implemented method for performing a review-by-exception process, the method comprising, via one or more processors of a computing device:
accessing chromatography information generated via analyzing a sample using a mass spectrometry system, the chromatography information comprising at least one peak and at least one peak attribute for the at least one peak;
determining posterior probability information for the chromatography information;
generating an estimated peak model based on the posterior probability information;
determining a confidence indicator for the estimated peak model; and generating an exception for the at least one peak responsive to the confidence indicator being outside of an exception threshold.

9. The method of claim 8, the instructions, comprising generating at least one information assessment screen to present at least one graphical user interface (GUI) object to visually highlight the exception.

10. The method of claim 8, the estimated peak model determined using Markov chain Monte Carlo and nested sampling.

11. The method of claim 8, the posterior probability information generated via Bayesian probabilistic analysis.

12. The method of claim 8, the posterior probability information comprising posterior probability samples for the at least one peak attribute, the at least one peak attribute comprising at least one of retention time, quantity, width, or asymmetry.

13. The method of claim 8, the confidence indicator indicating a confidence that the estimated peak model models the chromatography information.

14. The method of claim 8, the confidence indicator comprising at least one error bar.

15. At least one non-transitory computer-readable storage medium comprising instructions that, when executed, cause a system to:
    access chromatography information generated via analyzing a sample using a mass spectrometry system, the chromatography information comprising at least one peak and at least one peak attribute for the at least one peak;
    determine posterior probability information for the chromatography information;
    generate an estimated peak model based on the posterior probability information;
    determine a confidence indicator for the estimated peak model; and
    generate an exception for the at least one peak responsive to the confidence indicator being outside of an exception threshold.

16. The at least one non-transitory computer-readable storage medium of claim 15, the instructions, when executed, cause the system to generate at least one information assessment screen to present at least one graphical user interface (GUI) object to visually highlight the exception.

17. The at least one non-transitory computer-readable storage medium of claim 15, the estimated peak model determined using Markov chain Monte Carlo and nested sampling.

18. The at least one non-transitory computer-readable storage medium of claim 15, the posterior probability information generated via Bayesian probabilistic analysis.

19. The at least one non-transitory computer-readable storage medium of claim 15, the posterior probability information comprising posterior probability samples for the at least one peak attribute, the at least one peak attribute comprising at least one of retention time, quantity, width, or asymmetry.

20. The at least one non-transitory computer-readable storage medium of claim 15, the confidence indicator indicating a confidence that the estimated peak model models the chromatography information.

* * * * *